United States Patent
Park et al.

(10) Patent No.: US 9,617,216 B2
(45) Date of Patent: Apr. 11, 2017

(54) ANTIFUNGAL OXODIHYDROPYRIDINECARBOHYDRAZIDE DERIVATIVE

(71) Applicant: Daewoong Pharmaceutical Co., Ltd., Gyeonggi-do (KR)

(72) Inventors: Joon Seok Park, Gyeonggi-do (KR); Youn Jung Yoon, Gyeonggi-do (KR); Chang Min Park, Daejeon (KR); Yun Soo Na, Gyeonggi-do (KR); Min Jae Cho, Gyeonggi-do (KR); Ho Bin Lee, Seoul (KR); Mi Ryeong Han, Gyeonggi-do (KR); Yeon Jung Park, Ulsan (KR); Ji Duck Kim, Gyeonggi-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/029,638

(22) PCT Filed: Oct. 21, 2014

(86) PCT No.: PCT/KR2014/009876
§ 371 (c)(1),
(2) Date: Apr. 15, 2016

(87) PCT Pub. No.: WO2015/060613
PCT Pub. Date: Apr. 30, 2015

(65) Prior Publication Data
US 2016/0304460 A1   Oct. 20, 2016

(30) Foreign Application Priority Data
Oct. 21, 2013   (KR) .................... 10-2013-0125626

(51) Int. Cl.
| | | |
|---|---|---|
| C07D 213/63 | (2006.01) | |
| C07D 401/04 | (2006.01) | |
| C07D 401/06 | (2006.01) | |
| C07D 401/12 | (2006.01) | |
| A61K 31/4412 | (2006.01) | |
| A61P 31/04 | (2006.01) | |
| C07D 213/82 | (2006.01) | |
| C07D 417/06 | (2006.01) | |
| C07D 487/04 | (2006.01) | |
| C07D 498/08 | (2006.01) | |
| C07D 471/04 | (2006.01) | |

(52) U.S. Cl.
CPC ......... C07D 213/82 (2013.01); C07D 213/63 (2013.01); C07D 401/04 (2013.01); C07D 401/06 (2013.01); C07D 401/12 (2013.01); C07D 417/06 (2013.01); C07D 471/04 (2013.01); C07D 487/04 (2013.01); C07D 498/08 (2013.01)

(58) Field of Classification Search
CPC .. C07D 213/64; C07D 221/04; C07D 401/06; C07D 401/12; A61K 31/4412
USPC ......... 546/261, 290; 514/332, 346; 544/261, 544/290
See application file for complete search history.

(56) References Cited

U.S. PATENT DOCUMENTS

2009/0143402 A1   6/2009   Simonsen et al.

FOREIGN PATENT DOCUMENTS

| CA | 2683159 A1 | 11/2008 |
|---|---|---|
| JP | 2010-524980 A | 7/2010 |
| WO | WO-99/62335 A1 | 12/1999 |
| WO | WO-2008/131779 A1 | 11/2008 |

OTHER PUBLICATIONS

Roemer et al. Cold Spring Harb Perspect Med 2014, 4, 1-14.*
Song et al. Crit Rev Microbiol, Early Online 1-34, 2015.*
Bosch et al. Annu. Rev. Phytopathol. 2014. 52:175-95.*
El-Hashash et al., "Action of Pyrazolones, Ethyl Cyanoacetate & Cyanoacetylhydrazide on the Michael Adducts of Acetylacetone with Dichlorochalkones", Indian Journal of Chemistry, vol. 16B, Nov. 1978, pp. 984-988.
Sunitha et al., "Synthesis, Characterisation and Antimicrobial Studies on Transition Metal Complexes of n'-[phenyl(methylphenyl-5-pyrazolyl)methylidene] pyridine-4-carbohydrazide", Int. J. Pharm. Biomed. Sci. vol. 3, No. 3, 2012, pp. 109-116.
Search Report and Written Opinion in International Application No. PCT/KR2014/009876 dated Feb. 6, 2015, 12 pages.
Stanczak et al., "Synthesis, Structure, and Antibacterial Activity of 4-Imino-1,4-dihydrocinnoline-3-carboxylic Acid and 4-Oxo-1,4-dihydrocinnoline-3-carboxylic Acid Derivatives as Isosteric Analogues of Quinolones", Arch. Pharm. Pharm. Med. Chem. 1, 2003, pp. 18-30.
Office Action in JP Application No. 2016-525103 dated Feb. 14, 2017, 2 pages.

* cited by examiner

*Primary Examiner* — Venkataraman Balasubramanian
(74) *Attorney, Agent, or Firm* — Marshall, Gerstein & Borun LLP

(57) ABSTRACT

The present invention relates to novel oxodihydropyridinecarbohydrazide derivatives with excellent antifungal activities, an antifungal composition containing the same, and its use for the prevention and treatment of fungal infectious diseases. The oxodihydropyridinecarbohydrazide derivatives of the present invention have excellent antifungal and fungicidal activities, and thus will be useful for the prevention and treatment of various fungal infections by *Candida* spp., *Aspergillus* spp., *Cryptococcus neoformans* and *Trichophyton* spp., etc. Additionally, the oxodihydropyridinecarbohydrazide derivatives of the present invention, unlike other fungicidal preparations, can be orally administered.

15 Claims, No Drawings

ANTIFUNGAL OXODIHYDROPYRIDINECARBOHYDRAZIDE DERIVATIVE

TECHNICAL FIELD

The present invention relates, in general, to a novel oxodihydropyridinecarbohydrazide derivative with excellent antifungal activities, an antifungal composition containing the same, and its use for the prevention and treatment of fungal infectious diseases.

BACKGROUND ART

Recently, there have been a growing number of reports on serious fungal infections in immunocompromised cancer patients undergoing chemotherapies, organ transplant recipients, AIDS patients, etc. Most of the fungal infections are known to be caused by opportunistic pathogens such as *Candida* spp., *Aspergillus* spp. and *Cryptococcus neoformans*. Accordingly, for the future elderly society, development of medical countermeasures against emerging infectious diseases caused by pathogens including resistant bacteria will become an important issue.

The number of antifungal agents available at present is much less than that of antibiotics used for the treatment of bacterial infections. Examples of the antifungal agents developed so far include polyene antifungals such as amphotericin B or azole antifungals such as fluconazole, itraconazole, voriconazole, posaconazole, etc. However, the appearance of azole-resistant fungi has become a problem. Recently, cyclic hexapeptide type echinocandins from natural products (caspofungin, micafungin, and anidulafungin) have been developed as a new class of antifungals, 1,3-β-glucan synthase.

Additionally, benzimidazole compounds have been widely used as therapeutic agents such as parasiticides, antifungals, antiulcer drugs, etc., and thiabendazole, the representative benzimidazole antifungal, is known to have a structure similar to those of benzimidazole compounds. Procodazol, being a benzimidazole derivative, has a broad spectrum in the treatment of parasitic or fungal infections. Formulations containing the compound as an active ingredient, when orally administered, exhibit antifungal effects against infections caused by dermatomycoses such as Paracoccidioidomycosis and Histoplasmosis. Furthermore, benzimidazole compounds containing an aryl group or heteroarylalkanoic acid have been developed as non-steroid anti-inflammatory agents.

The antifungal agents may be classified into fungistatics and fungicides depending on the effects of their actions. Generally, fungicidal agents have a high clinical value due to their rapid and strong actions. Amphotericin B and echinocandins are known to be effective for the treatment of systemic mycoses. However, these fungicidal agents have only a limited use as they can be used in the form of injection only, and thus there is an unmet need for the development of a fungicidal agent for oral administration.

DISCLOSURE

Technical Problem

The inventors of the present invention, while endeavoring to find a compound useful as an antifungal agent, have found that the novel compound represented by Chemical Formula 1 as described in the specification of the present invention has an excellent antifungal effect, thereby completing the present invention.

Technical Solution

An objective of the present invention is to provide a novel oxodihydropyridinecarbohydrazide derivative compound with excellent antifungal effect, and a pharmaceutically acceptable salt thereof.

Another objective of the present invention is to provide a pharmaceutical composition containing the above compound as an active ingredient, or a pharmaceutical composition containing the above compound as an active ingredient for the prevention or treatment of fungal infectious diseases.

A further objective of the present invention is to provide an antifungal composition containing the above compound as an active ingredient.

A still further objective of the present invention is to provide a method for the prevention or treatment of fungal infectious diseases including administering a composition containing a compound or a pharmaceutically acceptable salt thereof as an active ingredient to a subject with a fungal infectious disease or a subject suspected of having the same.

Advantageous Effects

The novel antifungal oxodihydropyridinecarbohydrazide derivative of the present invention has excellent antifungal and fungicidal activities, and thus will be useful for the prevention and treatment of various fungal infections caused by agents such as *Candida* spp., *Aspergillus* spp., *Cryptococcus neoformans* and *Trichophyton* spp. Additionally, the pyridinylhydrazide derivative of the present invention is advantageous in that it can be orally administered unlike other fungicidal agents.

Best Mode

In order to achieve the above objectives, the present invention provides a compound represented by Chemical Formula 1 below, or a pharmaceutically acceptable salt thereof.

[Chemical Formula 1]

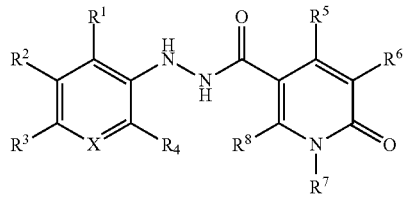

In the above Chemical Formula 1, $R^1$ is hydrogen; or halogen, $R^2$ is hydrogen; halogen; cyano; or $C_{1-4}$ haloalkyl, $R^3$ is hydrogen; halogen; cyano; $C_{1-4}$ alkoxy; $C_{1-4}$ haloalkyl or $C_{1-4}$ haloalkylsulfonyl, X is carbon; or nitrogen, wherein when X is carbon, then said X is unsubstituted or substituted with halogen, $R^4$ is hydrogen; halogen; $C_{1-4}$ alkyl; or is connected to $R^7$ to form

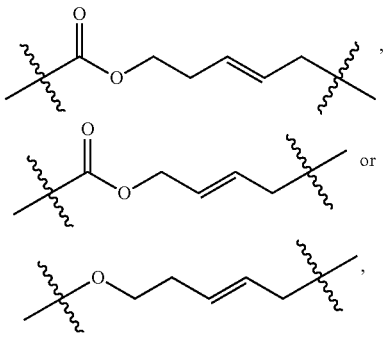

$R^5$ is hydrogen; halogen; or $C_{1-4}$ haloalkylphenylamino, $R^6$ is hydrogen; halogen; pyridinyl; or phenyl unsubstituted or substituted with halogen, cyano, or $C_{1-4}$ haloalkyl, $R^7$ is phenoxyethyl substituted with one to three same or different halogen atoms; phenoxyethyl substituted with $C_{1-4}$ haloalkyl; ethyl substituted with halophenyl; $C_{1-4}$ alkoxyethyl; morpholinoethyl; $C_{1-4}$ haloalkylphenylpiperazinylethyl; halophenyl; $C_{1-4}$ haloalkylphenyl; cyclohexylmethyl; thiazolylmethyl; $C_{1-4}$ haloalkylpyridinylmethyl; $C_{1-4}$ alkyl; dimethylaminocarbonylmethyl; $C_{1-4}$ haloalkylphenylacetamido; or oxotrifluoromethylphenylethyl, and $R^8$ is hydrogen; or is connected to $R^7$ to form $C_{1-3}$ alkylene.

Preferably, $R^1$ is hydrogen; chloro; or fluoro.

Additionally, preferably, $R^2$ is hydrogen; chloro; fluoro; cyano; or trifluoromethyl.

Additionally, preferably, $R^3$ is hydrogen; chloro; fluoro; cyano; methoxy; trifluoromethyl; or trifluoromethylsulfonyl.

Additionally, preferably, $R^4$ is hydrogen; fluoro; or methyl.

Additionally, preferably, $R^5$ is hydrogen; chloro; or trifluoromethylphenylamino.

Additionally, preferably, $R^6$ is hydrogen; chloro; pyridinyl; chlorophenyl; fluorophenyl; cyanophenyl; or trifluoromethylphenyl.

Additionally, preferably, $R^7$ is phenoxyethyl substituted with dichloro, chloro, or fluoro; trifluoromethylphenoxyethyl; chlorophenethyl; fluorophenethyl; methoxyethyl; morpholinoethyl; trifluoromethylphenylpiperazinylethyl; chlorophenyl; fluorophenyl; trifluoromethylphenyl; cyclohexylmethyl; thiazolylmethyl; trifluoromethylpyridinylmethyl; methyl; dimethylaminocarbonylmethyl; fluoromethylphenylacetamido; or oxotrifluoromethylphenylethyl.

Additionally, preferably, X is carbon, said X being substituted with fluoro.

Additionally, preferably, when X is nitrogen, $R^1$ is hydrogen, $R^2$ is hydrogen or fluoro, $R^3$ is fluoro or methoxy, $R^4$ is hydrogen; fluoro; or methyl, $R^5$ is hydrogen, $R^6$ is hydrogen; chlorophenyl; fluorophenyl; cyanophenyl; or trifluoromethylphenyl, and $R^7$ is chlorophenyl; or methyl.

Additionally, preferably, $R^8$ is hydrogen; or connected to $R^7$ to form propylene.

Preferred examples of the compounds according to the present invention are shown below:
1) N'-(2-fluorophenyl)-1-methyl-6-oxo-1,6-dihydropyridine-3-carbohydrazide,
2) N'-(3-fluorophenyl)-1-methyl-6-oxo-1,6-dihydropyridine-3-carbohydrazide,
3) N'-(4-fluorophenyl)-1-methyl-6-oxo-1,6-dihydropyridine-3-carbohydrazide,
4) N'-(3-chlorophenyl)-1-methyl-6-oxo-1,6-dihydropyridine-3-carbohydrazide,
5) N'-(4-chlorophenyl)-1-methyl-6-oxo-1,6-dihydropyridine-3-carbohydrazide,
6) N'-(3-cyanophenyl)-1-methyl-6-oxo-1,6-dihydropyridine-3-carbohydrazide,
7) N'-(4-cyanophenyl)-1-methyl-6-oxo-1,6-dihydropyridine-3-carbohydrazide,
8) 1-methyl-6-oxo-N'-(3-(trifluoromethyl)phenyl)-1,6-dihydropyridine-3-carbohydrazide,
9) 1-methyl-6-oxo-N'-(4-(trifluoromethyl)phenyl)-1,6-dihydropyridine-3-carbohydrazide,
10) 1-methyl-6-oxo-N'-(4-(trifluoromethylsulfonyl)phenyl)-1,6-dihydropyridine-3-carbohydrazide,
11) N'-(2,4-difluorophenyl)-1-methyl-6-oxo-1,6-dihydropyridine-3-carbohydrazide,
12) N'-(3,4-difluorophenyl)-1-methyl-6-oxo-1,6-dihydropyridine-3-carbohydrazide,
13) N'-(3,5-difluorophenyl)-1-methyl-6-oxo-1,6-dihydropyridine-3-carbohydrazide,
14) N'-(3,4-dichlorophenyl)-1-methyl-6-oxo-1,6-dihydropyridine-3-carbohydrazide,
15) N'-(2,4-dichlorophenyl)-1-methyl-6-oxo-1,6-dihydropyridine-3-carbohydrazide,
16) N'-(4-chloro-3-fluorophenyl)-1-methyl-6-oxo-1,6-dihydropyridine-3-carbohydrazide,
17) N'-(3-chloro-4-fluorophenyl)-1-methyl-6-oxo-1,6-dihydropyridine-3-carbohydrazide,
18) N'-(6-fluoropyridine-3-yl)-1-methyl-6-oxo-1,6-dihydropyridine-3-carbohydrazide,
19) N'-(2,6-difluoropyridine-3-yl)-1-methyl-6-oxo-1,6-dihydropyridine-3-carbohydrazide,
20) N'-(6-fluoro-2-methylpyridine-3-yl)-1-methyl-6-oxo-1,6-dihydropyridine-3-carbohydrazide,
21) N'-(5-fluoro-6-methoxypyridine-3-yl)-1-methyl-6-oxo-1,6-dihydropyridine-3-carbohydrazide,
22) 4-chloro-N'-(3-fluorophenyl)-1-methyl-6-oxo-1,6-dihydropyridine-3-carbohydrazide,
23) 4-chloro-N'-(4-fluorophenyl)-1-methyl-6-oxo-1,6-dihydropyridine-3-carbohydrazide,
24) 5-chloro-N'-(3-fluorophenyl)-1-methyl-6-oxo-1,6-dihydropyridine-3-carbohydrazide,
25) 5-chloro-N'-(4-fluorophenyl)-1-methyl-6-oxo-1,6-dihydropyridine-3-carbohydrazide,
26) 5-chloro-N'-(3-chlorophenyl)-1-methyl-6-oxo-1,6-dihydropyridine-3-carbohydrazide,
27) 5-chloro-N'-(4-chlorophenyl)-1-methyl-6-oxo-1,6-dihydropyridine-3-carbohydrazide,
28) 5-chloro-N'-(3-cyanophenyl)-1-methyl-6-oxo-1,6-dihydropyridine-3-carbohydrazide,
29) 5-chloro-N'-(4-cyanophenyl)-1-methyl-6-oxo-1,6-dihydropyridine-3-carbohydrazide,
30) 5-chloro-N'-(2,4-difluorophenyl)-1-methyl-6-oxo-1,6-dihydropyridine-3-carbohydrazide,
31) 5-chloro-N'-(3,4-difluorophenyl)-1-methyl-6-oxo-1,6-dihydropyridine-3-carbohydrazide,
32) 5-chloro-N'-(3,5-difluorophenyl)-1-methyl-6-oxo-1,6-dihydropyridine-3-carbohydrazide,
33) 7-chloro-N'-(3-fluorophenyl)-5-oxo-1,2,3,5-tetrahydroindolizine-8-carbohydrazide, 34) 7-chloro-N'-(4-fluorophenyl)-5-oxo-1,2,3,5-tetrahydroindolizine-8-carbohydrazide,
35) N'-(3-fluorophenyl)-1-methyl-6-oxo-4-(4-(trifluoromethyl)phenylamino)-1,6-dihydropyridine-3-carbohydrazide,
36) N'-(4-fluorophenyl)-1-methyl-6-oxo-4-(4-(trifluoromethyl)phenylamino)-1,6-dihydropyridine-3-carbohydrazide,
37) N'-(5-fluoro-6-methoxypyridine-3-yl)-5-(4-fluorophenyl)-1-methyl-6-oxo-1,6-dihydropyridine-3-carbohydrazide,
38) 5-(4-chlorophenyl)-N'-(5-fluoro-6-methoxypyridine-3-yl)-1-methyl-6-oxo-1,6-dihydropyridine-3-carbohydrazide,
39) N'-(5-fluoro-6-methoxypyridine-3-yl)-1-methyl-6-oxo-5-(4-(trifluoromethyl)phenyl)-1,6-dihydropyridine-3-carbohydrazide,
40) 5-(4-cyanophenyl)-N'-(5-fluoro-6-methoxypyridine-3-yl)-1-methyl-6-oxo-1,6-dihydropyridine-3-carbohydrazide,
41) N'-(3-fluorophenyl)-1-methyl-6-oxo-5-(pyridine-2-yl)-1,6-dihydropyridine-3-carbohydrazide,
42) 1-(2-fluorophenyl)-N'-(3-fluorophenyl)-6-oxo-1,6-dihydropyridine-3-carbohydrazide,
43) N',1-Bis(3-fluorophenyl)-6-oxo-1,6-dihydropyridine-3-carbohydrazide,
44) N'-(3-fluorophenyl)-1-(4-fluorophenyl)-6-oxo-1,6-dihydropyridine-3-carbohydrazide,
45) N'-(4-fluorophenyl)-6-oxo-1-(4-(trifluoromethyl)phenyl)-1,6-dihydropyridine-3-carbohydrazide,
46) N'-(4-fluorophenyl)-6-oxo-1-(3-(trifluoromethyl)phenyl)-1,6-dihydropyridine-3-carbohydrazide,
47) 1-(3-chlorophenyl)-N'-(4-fluorophenyl)-6-oxo-1,6-dihydropyridine-3-carbohydrazide,
48) 1-(3-chlorophenyl)-N'-(5-fluoro-6-methoxypyridine-3-yl)-6-oxo-1,6-dihydropyridine-3-carbohydrazide,
49) N'-(2,4-difluorophenyl)-6-oxo-1-(thiazol-4-ylmethyl)-1,6-dihydropyridine-3-carbohydrazide,
50) N'-(3-fluorophenyl)-6-oxo-1-((6-(trifluoromethyl)pyridine-3-yl)methyl)-1,6-dihydropyridine-3-carbohydrazide,
51) N'-(4-fluorophenyl)-6-oxo-1-((6-(trifluoromethyl)pyridine-3-yl)methyl)-1,6-dihydropyridine-3-carbohydrazide,
52) N'-(3,4-difluorophenyl)-6-oxo-1-((6-(trifluoromethyl)pyridine-3-yl)methyl)-1,6-dihydropyridine-3-carbohydrazide,
53) N'-(3,5-difluorophenyl)-6-oxo-1-((6-(trifluoromethyl)pyridine-3-yl)methyl)-1,6-dihydropyridine-3-carbohydrazide,
54) N'-(2,4-difluorophenyl)-6-oxo-1-((6-(trifluoromethyl)pyridine-3-yl)methyl)-1,6-dihydropyridine-3-carbohydrazide,
55) N'-(3-fluorophenyl)-6-oxo-1-(2-(4-(4-(trifluoromethyl)phenyl)piperazin-1-yl)ethyl)-1,6-dihydropyridine-3-carbohydrazide,
56) N'-(4-fluorophenyl)-6-oxo-1-(2-(4-(4-(trifluoromethyl)phenyl)piperazin-1-yl)ethyl)-1,6-dihydropyridine-3-carbohydrazide,
57) 1-(3-chlorophenethyl)-N'-(3-fluorophenyl)-6-oxo-1,6-dihydropyridine-3-carbohydrazide,
58) 1-(4-chlorophenethyl)-N'-(3-fluorophenyl)-6-oxo-1,6-dihydropyridine-3-carbohydrazide,
59) 1-(2-fluorophenethyl)-N'-(3-fluorophenyl)-6-oxo-1,6-dihydropyridine-3-carbohydrazide,
60) 1-(4-fluorophenethyl)-N'-(3-fluorophenyl)-6-oxo-1,6-dihydropyridine-3-carbohydrazide,
61) 1-(2-(2-fluorophenoxy)ethyl)-N'-(3-fluorophenyl)-6-oxo-1,6-dihydropyridine-3-carbohydrazide,
62) 1-(2-(4-chlorophenoxy)ethyl)-N'-(3-fluorophenyl)-6-oxo-1,6-dihydropyridine-3-carbohydrazide,
63) N'-(3-fluorophenyl)-6-oxo-1-(2-(3-(trifluoromethyl)phenoxy)ethyl)-1,6-dihydropyridine-3-carbohydrazide,
64) 1-(2-(2,4-dichlorophenoxy)ethyl)-N'-(3-fluorophenyl)-6-oxo-1,6-dihydropyridine-3-carbohydrazide,
65) 1-(2-(4-fluorophenoxy)ethyl)-N'-(3-fluorophenyl)-6-oxo-1,6-dihydropyridine-3-carbohydrazide,
66) 1-(cyclohexylmethyl)-N'-(3-fluorophenyl)-6-oxo-1,6-dihydropyridine-3-carbohydrazide,
67) 1-(cyclohexylmethyl)-N'-(4-fluorophenyl)-6-oxo-1,6-dihydropyridine-3-carbohydrazide,
68) N'-(3-fluorophenyl)-6-oxo-1-(2-oxo-2-(4-(trifluoromethyl)phenyl)ethyl)-1,6-dihydropyridine-3-carbohydrazide,
69) N'-(4-fluorophenyl)-6-oxo-1-(2-oxo-2-(4-(trifluoromethyl)phenyl)ethyl)-1,6-dihydropyridine-3-carbohydrazide,
70) N'-(3,4-difluorophenyl)-6-oxo-1-(2-oxo-2-(4-(trifluoromethyl)phenyl)ethyl)-1,6-dihydropyridine-3-carbohydrazide,
71) 2-(5-(2-(3-fluorophenyl)hydrazinecarbonyl)-2-oxopyridine-1(2H)-yl)-N-(4-(trifluoromethyl)phenyl)acetamide,
72) 2-(5-(2-(4-fluorophenyl)hydrazinecarbonyl)-2-oxopyridine-1(2H)-yl)-N-(4-(trifluoromethyl)phenyl)acetamide,
73) N'-(3-fluorophenyl)-1-(2-morpholinoethyl)-6-oxo-1,6-dihydropyridine-3-carbohydrazide,
74) N'-(4-fluorophenyl)-1-(2-morpholinoethyl)-6-oxo-1,6-dihydropyridine-3-carbohydrazide,
75) 2-(5-(2-(3-fluorophenyl)hydrazine-1-carbonyl)-2-oxopyridine-1(2H)-yl)-N,N-dimethylacetamide,
76) N'-(3-fluorophenyl)-1-(2-methoxyethyl)-6-oxo-1,6-dihydropyridine-3-carbohydrazide,
77) 2-(5-(2-(4-fluorophenyl)hydrazinecarbonyl)-2-oxopyridine-1(2H)-yl)-N,N-dimethylacetamide,
78) N'-(4-fluorophenyl)-1-(2-methoxyethyl)-6-oxo-1,6-dihydropyridine-3-carbohydrazide,
79) ($1^5$E,10E)-$5^5$-fluoro-$1^1$,$1^2$-dihydro-7-oxa-3,4-diaza-1(5,1)-pyridina-5(1,2)-benzenacyclododecaphan-10-ene-$1^2$,2,6-trione,
80) ($1^5$E,9E)-$1^1$,$1^2$-dihydro-7-oxa-3,4-diaza-1(5,1)-pyridina-5(1,2)-benzenacycloundecaphan-9-ene-$1^2$,2,6-trione, and
81) ($1^5$E,9E)-$1^1$,$1^2$-dihydro-6-oxa-3,4-diaza-1(5,1)-pyridina-5(1,2)-benzenacycloundecaphan-9-ene-$1^2$,2-dione.

The compound represented by Chemical Formula 1 of the present invention may be provided in the form of a pharmaceutically acceptable salt derived from an inorganic or organic acid. Examples of the salts to be used in the present invention may include inorganic or organic salts known in the art of antifungal agents, and they may be manufactured by a known method. Examples of the salts are inorganic acids such as hydrochloric acid and nitric acid; sulfonic acid such as methanesulfonic acid; or an acid addition salt formed by an organic carbonic acid such as oxalic acid.

Additionally, the compound represented by Chemical Formula 1 of the present invention may include a hydrate and a solvate that can be manufactured therefrom.

Additionally, the present invention provides a pharmaceutical composition, a pharmaceutical composition for the prevention or treatment of fungal infectious diseases, and an antifungal composition containing a compound represented by Chemical Formula 1, or a pharmaceutically acceptable salt thereof as an active ingredient, respectively.

Because the compound represented by Chemical Formula 1, a pharmaceutically acceptable salt thereof, an isomer thereof, a hydrate thereof, and a solvate thereof have an excellent fungicidal activity along with an excellent antifungal activity, they may be useful for the prevention and treatment of various types fungal infections such as infections by *Candida* spp., *Aspergillus* spp., *Cryptococcus neoformans* and *Trichophyton* spp. Accordingly, the present invention provides a pharmaceutical composition, a pharmaceutical composition for the prevention or treatment of fungal infectious diseases, and an antifungal composition containing a compound selected from the group consisting of a compound represented by Chemical Formula 1, a pharmaceutically acceptable salt thereof, an isomer thereof, a hydrate thereof, and a solvate thereof, as an active ingredient. In particular, the antifungal composition may include a pharmaceutically acceptable carrier or vehicle as well.

The antifungal composition of the present invention may be formulated into various types via a conventional method in the art by mixing the compound of the present invention with a pharmaceutically acceptable inert carrier or vehicle suitable for oral, parenteral, or topical administration. In particular, the antifungal composition of the present invention has a fungicidal activity and may be orally administered.

Examples of the preparations for oral administration may include tablets, capsules, etc., which may include, in addition to the active ingredient, a diluent (e.g., lactose, dextrose, sucrose, mannitol, sorbitol, cellulose or glycine, etc.), a lubricant (e.g., silica, talc, stearic acid and magnesium stearate or calcium stearate, or polyethylene glycol, etc.) or a binder (e.g., magnesium aluminum silicate, starch paste, gelatin, tragacanth, methylcellulose, sodium carboxymethyl cellulose or polyvinyl pyrrolidone, etc.), and may further include starch, agar, a disintegrating agent such as alginic acid or sodium alginate, an azeotropic mixture, an absorbent, a coloring agent, a flavoring agent, a sweetener, etc., as necessary.

In an aspect of the present invention, there is provided a method for the prevention or treatment of fungal infectious diseases including administering a composition containing a compound represented by Chemical Formula 1 above or a pharmaceutically acceptable salt thereof as an active ingredient to a subject with a fungal infectious disease or a subject suspected of having the same.

The above subject refers to all animals including humans with a fungal infectious disease or a potential of having the same. The above compound may be administered in the form of a pharmaceutical composition, orally or parenterally. Additionally, the preferred dosage of the compound of the present invention may vary depending on various factors such as health status, body weight, and severity of disease(s) of a subject, drug types, administration routes and duration, and may be appropriately determined by one of ordinary skill in the art. Preferably, the compound of the present invention may be administered for the treatment of mammals including humans with fungal infections or with a potential of having the same in the amount of 0.05 mg/kg/day to 200 mg/kg/day, more preferably 0.05 mg/kg/day to 100 mg/kg/day, orally or via an injection.

The term 'administration', as used herein, refers to the introduction of a compound or composition of the present invention into a subject in a suitable manner. Any administration route may be taken orally or via various parenteral routes, as long as it allows the composition to reach a target tissue in the body, in particular, oral, rectal, local, intravenous, intraperitoneal, intramuscular, intra-arterial, transdermal, intranasal, inhalative or intravascular routes via a conventional method.

Additionally, the present invention provides a method for manufacturing a compound of Chemical Formula 1 or a pharmaceutically acceptable salt thereof.

Additionally, the present invention provides a use of a composition containing a compound of Chemical Formula 1 or a pharmaceutically acceptable salt thereof as an active ingredient for the prevention or treatment of fungal infectious diseases.

Additionally, in the present invention, the compound of Chemical Formula 1 may be obtained by reacting a compound of Chemical Formula 2 with a compound of Chemical Formula 3.

[Chemical Formula 2]

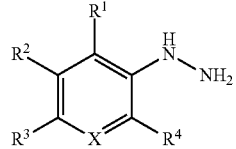

[Chemical Formula 3]

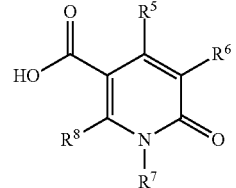

wherein, in above Chemical Formulas, $R^1$ through $R^8$ and X are the same as defined above.

The manufacturing method of the present invention is schematically illustrated in Reaction Scheme 1 below.

[Reaction Scheme 1]

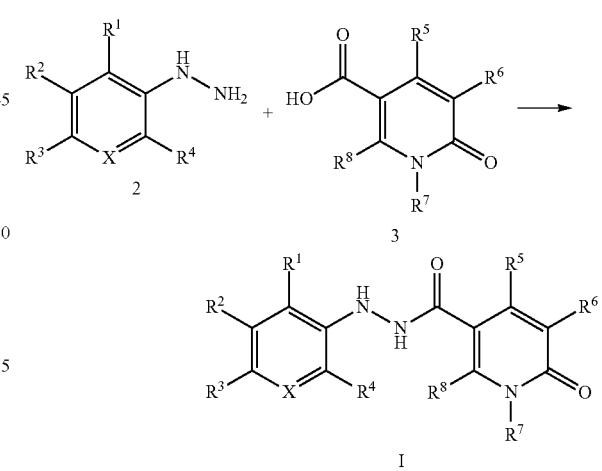

In Reaction Scheme 1 above, $R^1$ through $R^8$ and X are the same as defined above, and each reaction is preferably performed in a reaction solvent.

The compounds represented by Chemical Formula 2 and Chemical Formula 3, being known compounds, can be manufactured by known methods, and may be purchased from a commercial market. The carboxylic acid of Chemical Formula 3 may be used after converting it to methyl carboxylate or chloroacyl group.

Additionally, when the substituent $R^5$ in a compound of Chemical Formula 3 is $C_{1-4}$ haloalkylphenylamino, the compound of Chemical Formula 3 may be used after manufacturing it by a method shown in Reaction Scheme 2 below.

[Reaction Scheme 2]

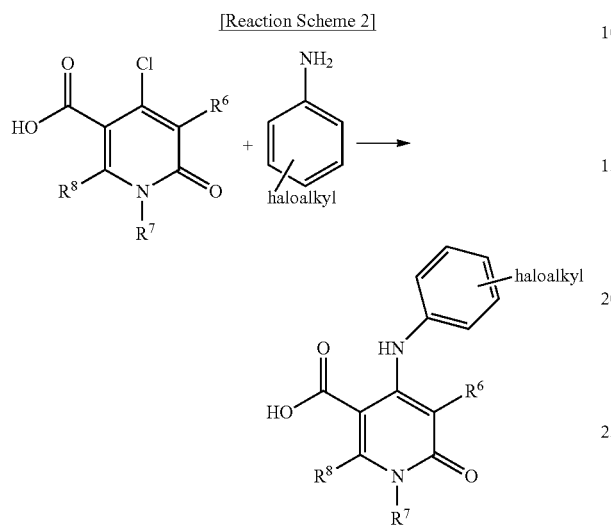

In Reaction Scheme 2 above, $R^6$ through $R^8$ are the same as defined above.

Preferably, the reaction in Reaction Scheme 2 above is performed in the presence of a solvent in a basic condition. In particular, the reaction solvent is preferably a polar organic solvent, in particular, a polar solvent such as tetrahydrofuran. Additionally, the base to be used in the above reaction may be a conventional inorganic base or organic base, for example, an inorganic base such as lithium hexamethyldisilazide (LHMDS) or lithium diisopropylamide (LDA).

Additionally, the compound having $C_{1-4}$ haloalkylphenylamino as a substituent for $R^5$ among the compounds representing Chemical Formula 3 may be prepared by stirring at −78° C. to 50° C., preferably between room temperature and 50° C., for 30 minutes to 24 hours.

Additionally, when the substituent $R^6$ in a compound of Chemical Formula 3 is phenyl substituted with $C_{1-4}$ haloalkyl, the compound of Chemical Formula 3 may be used after manufacturing it by a method shown in Reaction Scheme 3 below.

[Reaction Scheme 3]

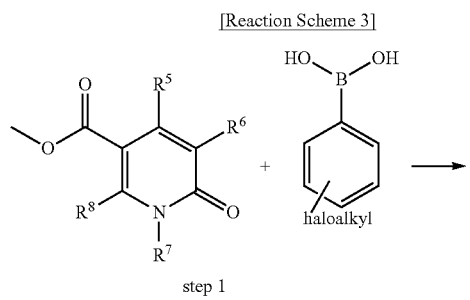

step 1

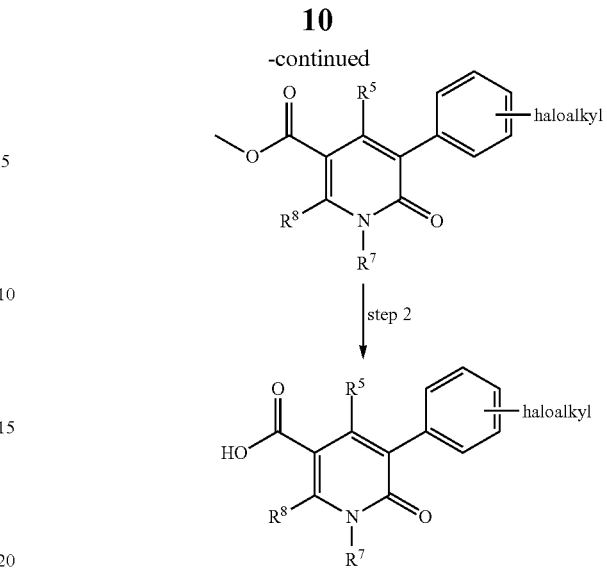

In Reaction Scheme 3 above, $R^5$, $R^7$, and $R^8$ are the same as defined above.

Step 1 in Reaction Scheme 3 above is a reaction occurring in a basic condition via Suzuki cross-coupling reaction using palladium catalyst. Preferably, the reaction solvent to be used is a polar organic solvent, and more preferably, polar solvents such as dimethylformamide, tetrahydrofuran, methanol, ethanol, dioxane or water. Additionally, the base to be used in the reaction may be a conventional inorganic base, for example, sodium carbonate ($Na_2CO_3$), sodium hydrogen carbonate ($NaHCO_3$), potassium carbonate ($K_2CO_3$) or cesium carbonate ($Cs_2CO_3$), etc.

Step 2 in Reaction Scheme 3 above is a reaction to convert a coupled compound from Suzuki reaction into carboxylic acid by hydrolysis.

Preferably, the reactions of Step 1 and Step 2 are carried out by heat-treatment at 0° C. to 200° C., and more preferably, 50° C. to 150° C., for 30 minutes to 24 hours, or via microwave irradiation, to thereby obtain a compound of Chemical Formula 3 wherein the $R^6$ substituent is phenyl substituted with $C_{1-4}$ haloalkyl.

The present invention will be explained in further details herein below with reference to Examples, however, they are disclosed for illustrative purposes and should not be construed as limiting the scope of the present invention.

Example 1: Preparation of N'-(2-fluorophenyl)-1-methyl-6-oxo-1,6-dihydropyridine-3-carbohydrazide 1-methyl-6-oxo-1,6-dihydropyridine-3-carboxylic acid (15.7 mg, 0.1 mmol) was dissolved in tetrahydrofuran (1 mL), cooled to 0° C., and sequentially added with 1-ethyl-3-(3-dimethylaminopropyl)carbodiimide (17.1 mg, 0.11 mmol), hydroxybenzotriazole (14.9 mg, 0.11 mmol), and triethylamine (27.9 µL, 0.2 mmol). After stirring at 0° C. for 30 minutes, the resulting mixture was added with (2-fluorophenyl)hydrazine (12.6 mg, 0.1 mmol) and 4-dimethylaminopyridine (2.4 mg, 0.02 mmol), and stirred at room temperature for 2 hours. Upon completion of the reaction, the solvent therein was removed, and the resultant was diluted with ethyl acetate, and washed with saturated sodium chloride solution. The resulting organic layer was collected, dried with magnesium sulfate and filtered, concentrated under reduced pressure, and subjected to column chromatography (developing solution, ethyl acetate:hexane=1:1) to obtain a title compound (17.0 mg, yield 65%).

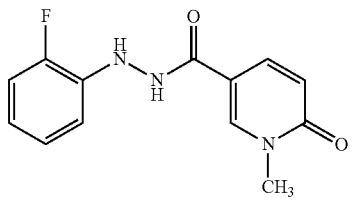 [SMILES: Cn1cc(C(=O)NNc2ccccc2F)ccc1=O]

$^1$H NMR (MeOH-d$_4$): δ 8.38 (s, 1H), 7.96 (d, 1H), 7.02 (m, 2H), 6.93 (t, 1H), 6.79 (m, 1H), 6.57 (d, 1H), 3.63 (s, 3H)

Example 2: Preparation of N'-(3-fluorophenyl)-1-methyl-6-oxo-1,6-dihydropyridine-3-carbohydrazide A title compound (18.0 mg, yield 69%) was obtained in the same manner as in Example 1 except that (3-fluorophenyl)hydrazine was used instead of (2-fluorophenyl)hydrazine.

$^1$H NMR (MeOH-d$_4$): δ 8.37 (d, 2H), 8.36-7.94 (m, 1H), 7.17-7.61 (m, 1H), 6.57-6.47 (m, 4H), 3.63 (s, 3H)

Example 3: Preparation of N'-(4-fluorophenyl)-1-methyl-6-oxo-1,6-dihydropyridine-3-carbohydrazide A title compound (14.9 mg, yield 57%) was obtained in the same manner as in Example 1 except that (4-fluorophenyl)hydrazine was used instead of (2-fluorophenyl)hydrazine.

$^1$H NMR (DMSO-d$_6$): δ 10.10 (s, 1H), 8.40 (s, 1H), 7.86 (d, 1H), 7.82 (s, 1H), 6.96 (t, 2H), 6.79 (m, 2H), 6.41 (d, 1H), 3.48 (s, 3H)

Example 4: Preparation of N'-(3-chlorophenyl)-1-methyl-6-oxo-1,6-dihydropyridine-3-carbohydrazide A title compound (17.8 mg, yield 64%) was obtained in the same manner as in Example 1 except that (3-chlorophenyl)hydrazine was used instead of (2-fluorophenyl)hydrazine.

$^1$H NMR (CDCl$_3$-d): δ 8.18 (s, 1H), 7.69 (d, 1H), 7.16 (t, 1H), 6.90-6.87 (m, 2H), 6.78-6.76 (m, 1H), 6.59 (d, 1H), 3.63 (s, 3H)

Example 5: Preparation of N'-(4-chlorophenyl)-1-methyl-6-oxo-1,6-dihydropyridine-3-carbohydrazide A title compound (20.8 mg, yield 75%) was obtained in the same manner as in Example 1 except that (4-chlorophenyl)hydrazine was used instead of (2-fluorophenyl)hydrazine.

$^1$H NMR (DMSO-d$_6$): δ 10.10 (s, 1H), 8.40 (s, 1H), 7.86 (d, 1H), 7.82 (s, 1H), 6.96 (t, 2H), 6.79 (m, 2H), 6.41 (d, 1H), 3.48 (s, 3H)

Example 6: Preparation of N'-(3-cyanophenyl)-1-methyl-6-oxo-1,6-dihydropyridine-3-carbohydrazide A title compound (20.7 mg, yield 77%) was obtained in the same manner as in Example 1 except that 3-hydrazinylbenzonitrile was used instead of (2-fluorophenyl)hydrazine.

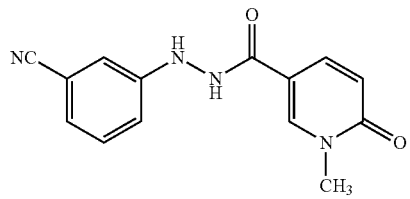 [SMILES: Cn1cc(C(=O)NNc2cccc(C#N)c2)ccc1=O]

$^1$H NMR (CDCl$_3$-d): δ 8.19 (s, 1H), 7.70 (d, 1H), 7.34 (t, 1H), 7.21-7.20 (m, 1H), 7.13-7.10 (m, 2H), 6.61 (d, 1H), 3.63 (s, 3H)

Example 7: Preparation of N'-(4-cyanophenyl)-1-methyl-6-oxo-1,6-dihydropyridine-3-carbohydrazide A title compound (21.2 mg, yield 79%) was obtained in the same manner as in Example 1 except that 4-hydrazinylbenzonitrile was used instead of (2-fluorophenyl)hydrazine.

$^1$H NMR (CDCl$_3$-d): δ 8.18 (s, 1H), 7.65 (d, 1H), 7.54 (d, 2H), 6.91 (d, 1H), 6.61 (d, 1H), 3.64 (s, 3H)

Example 8: Preparation of 1-methyl-6-oxo-N'-(3-(trifluoromethyl)phenyl)-1,6-dihydropyridine-3-carbohydrazide A title compound (21.5 mg, yield 69%) was obtained in the same manner as in Example 1 except that (3-(trifluoromethyl)phenyl)hydrazine was used instead of (2-fluorophenyl)hydrazine.

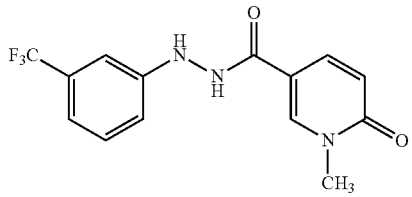 [SMILES: Cn1cc(C(=O)NNc2cccc(C(F)(F)F)c2)ccc1=O]

$^1$H NMR (CDCl$_3$-d): δ 8.18 (s, 1H), 7.70 (d, 1H), 7.35 (t, 1H), 7.17 (d, 1H), 7.10 (s, 1H), 7.05 (d, 2H), 6.59 (d, 1H), 3.61 (s, 3H)

Example 9: Preparation of 1-methyl-6-oxo-N'-(4-(trifluoromethyl)phenyl)-1,6-dihydropyridine-3-carbohydrazide A title compound (17.7 mg, yield 57%) was obtained in the same manner as in Example 1 except that (4-(trifluoromethyl)phenyl)hydrazine was used instead of (2-fluorophenyl)hydrazine.

$^1$H NMR (CDCl$_3$-d): δ 8.18 (s, 1H), 7.69 (d, 1H), 7.49 (d, 2H), 6.93 (d, 2H), 6.60 (d, 1H), 3.61 (s, 3H)

Example 10: Preparation of 1-methyl-6-oxo-N'-(4-((trifluoromethyl)sulfonyl)phenyl)-1,6-dihydropyridine-3-carbohydrazide A title compound (23.3 mg, yield 62%) was obtained in the same manner as in Example 1 except that (4-((trifluoromethyl)sulfonyl)phenyl)hydrazine was used instead of (2-fluorophenyl)hydrazine.

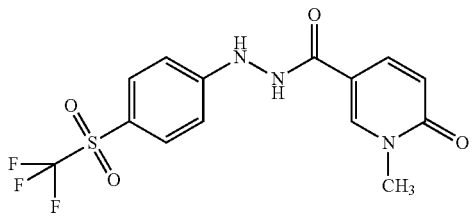 [SMILES: Cn1cc(C(=O)NNc2ccc(S(=O)(=O)C(F)(F)F)cc2)ccc1=O]

$^1$H NMR (MeOH-d$_4$): δ 8.39 (s, 1H), 7.96 (d, 1H), 7.57 (d, 1H), 7.55 (d, 1H), 7.20 (dd, 1H), 6.57 (d, 1H), 3.63 (s, 3H)

Example 11: Preparation of N'-(2,4-difluorophenyl)-1-methyl-6-oxo-1,6-dihydropyridine-3-carbohydrazide A title compound (15.1 mg, yield 54%) was obtained in the same manner as in Example 1 except that (2,4-difluorophenyl)hydrazine was used instead of (2-fluorophenyl)hydrazine.

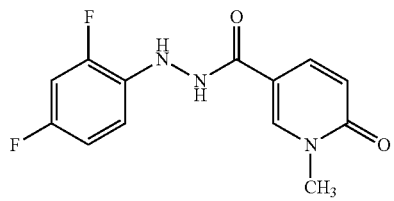 [SMILES: Cn1cc(C(=O)NNc2ccc(F)cc2F)ccc1=O]

$^1$H NMR (MeOH-d$_4$): δ 8.39 (s, 1H), 7.96 (d, 1H), 6.90 (d, 1H), 6.88 (d, 1H), 6.60 (dd, 1H), 6.57 (d, 1H), 3.63 (s, 3H)

Example 12: Preparation of N'-(3,4-difluorophenyl)-1-methyl-6-oxo-1,6-dihydropyridine-3-carbohydrazide A title compound (17.0 mg, yield 61%) was obtained in the same manner as in Example 1 except that (3,4-difluorophenyl)hydrazine was used instead of (2-fluorophenyl)hydrazine.

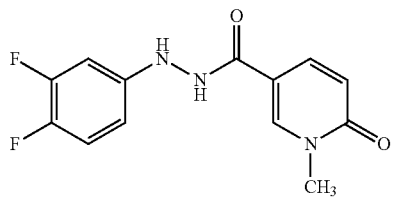 [SMILES: Cn1cc(C(=O)NNc2ccc(F)c(F)c2)ccc1=O]

$^1$H NMR (MeOH-d$_4$): δ 8.39 (s, 1H), 7.92 (d, 1H), 7.31 (d, 1H), 6.95 (d, 1H), 6.77 (dd, 1H), 6.57 (d, 1H), 3.64 (s, 3H)

Example 13: Preparation of N'-(3,5-difluorophenyl)-1-methyl-6-oxo-1,6-dihydropyridine-3-carbohydrazide A title compound (17.6 mg, yield 63%) was obtained in the same manner as in Example 1 except that (3,5-difluorophenyl)hydrazine was used instead of (2-fluorophenyl)hydrazine.

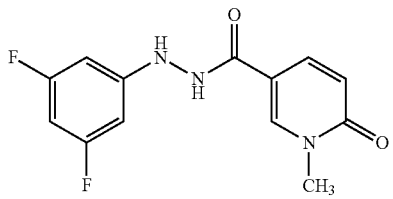 [SMILES: Cn1cc(C(=O)NNc2cc(F)cc(F)c2)ccc1=O]

$^1$H NMR (MeOH-d$_4$): δ 8.39 (s, 1H), 7.96 (d, 1H), 6.77 (d, 1H), 6.75 (d, 1H), 6.57 (d, 1H), 6.15 (dd, 1H), 3.63 (s, 3H)

Example 14: Preparation of N'-(3,4-dichlorophenyl)-1-methyl-6-oxo-1,6-dihydropyridine-3-carbohydrazide A title compound (22.5 mg, yield 72%) was obtained in the same manner as in Example 1 except that (3,4-dichlorophenyl)hydrazine was used instead of (2-fluorophenyl)hydrazine.

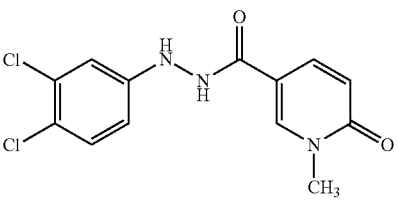 [SMILES: Cn1cc(C(=O)NNc2ccc(Cl)c(Cl)c2)ccc1=O]

$^1$H NMR (MeOH-d$_4$): δ 8.39 (s, 1H), 7.96 (d, 1H), 7.29 (d, 1H), 6.95 (d, 1H), 6.77 (dd, 1H), 6.57 (d, 1H), 3.63 (s, 3H)

Example 15: Preparation of N'-(2,4-dichlorophenyl)-1-methyl-6-oxo-1,6-dihydropyridine-3-carbohydrazide A title compound (19.0 mg, yield 61%) was obtained in the same manner as in Example 1 except that (2,4-dichlorophenyl)hydrazine was used instead of (2-fluorophenyl)hydrazine.

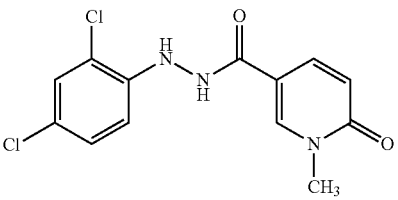 [SMILES: Cn1cc(C(=O)NNc2ccc(Cl)cc2Cl)ccc1=O]

$^1$H NMR (MeOH-d$_4$): δ 8.38 (s, 1H), 7.95 (d, 1H), 6.90 (d, 1H), 6.87 (d, 1H), 6.60 (dd, 1H), 6.57 (d, 1H), 3.62 (s, 3H)

Example 16: Preparation of N'-(4-chloro-3-fluorophenyl)-1-methyl-6-oxo-1,6-dihydropyridine-3-carbohydrazide A title compound (16.9 mg, yield 57%) was obtained in the same manner as in Example 1 except that (4-chloro-3-fluorophenyl)hydrazine was used instead of (2-fluorophenyl)hydrazine.

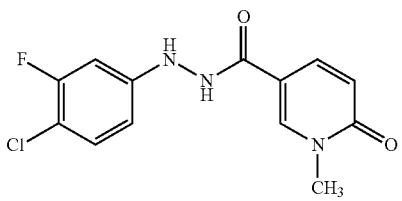 [SMILES: Cn1cc(C(=O)NNc2ccc(Cl)c(F)c2)ccc1=O]

¹H NMR (CDCl₃-d): δ8.16 (s, 1H), 7.64 (d, 2H), 6.69 (d, 2H), 6.62 (t, 1H), 3.62 (s, 3H)

Example 17: Preparation of N'-(3-chloro-4-fluorophenyl)-1-methyl-6-oxo-1,6-dihydropyridine-3-carbohydrazide A title compound (15.4 mg, yield 52%) was obtained in the same manner as in Example 1 except that (3-chloro-4-fluorophenyl)hydrazine was used instead of (2-fluorophenyl)hydrazine.

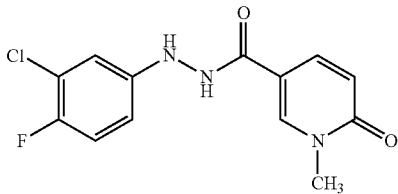 [SMILES: Cn1cc(C(=O)NNc2ccc(F)c(Cl)c2)ccc1=O]

¹H NMR (CDCl₃-d): δ8.17 (s, 1H), 7.66 (d, 1H), 7.03 (t, 1H), 6.94-6.92 (m, 1H), 6.77-6.74 (m, 1H), 6.61-6.59 (m, 1H), 3.62 (s, 3H)

Example 18: Preparation of N'-(6-fluoropyridine-3-yl)-1-methyl-6-oxo-1,6-dihydropyridine-3-carbohydrazide A title compound (16.8 mg, yield 64%) was obtained in the same manner as in Example 1 except that 2-fluoro-5-hydrazinylpyridine was used instead of (2-fluorophenyl)hydrazine.

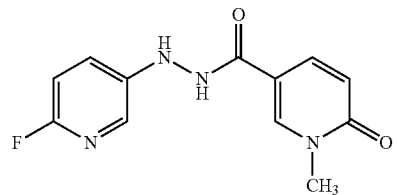 [SMILES: Cn1cc(C(=O)NNc2ccc(F)nc2)ccc1=O]

¹H NMR (MeOH-d₄): δ 8.35 (d, 1H), 7.71 (dd, 1H), 7.53 (d, 1H), 7.30 (d, 1H), 7.09 (dd, 1H), 6.55 (d, 1H), 3.60 (s, 3H)

Example 19: Preparation of N'-(2,6-difluoropyridine-3-yl)-1-methyl-6-oxo-1,6-dihydropyridine-3-carbohydrazide A title compound (21.0 mg, yield 75%) was obtained in the same manner as in Example 1 except that 2,6-fluoro-5-hydrazinylpyridine was used instead of (2-fluorophenyl)hydrazine.

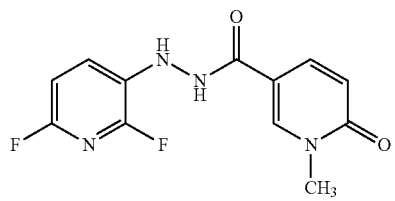

¹H NMR (CDCl₃-d): δ 8.46 (s, 1H), 8.40-8.30 (m, 1H), 8.02 (d, 1H), 7.03 (s, 1H), 6.58 (d, 1H), 3.64 (s, 1H)

Example 20: Preparation of N'-(6-fluoro-2-methylpyridine-3-yl)-1-methyl-6-oxo-1,6-dihydropyridine-3-carbohydrazide A title compound (21.3 mg, yield 77%) was obtained in the same manner as in Example 1 except that 6-fluoro-2-methyl-5-hydrazinylpyridine was used instead of (2-fluorophenyl)hydrazine.

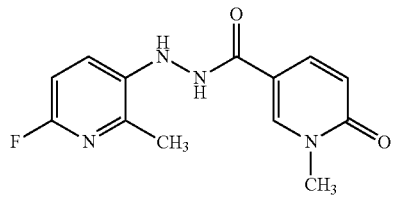 [SMILES: Cn1cc(C(=O)NNc2ccc(F)nc2F)ccc1=O]

¹H NMR (DMSO-d₆) δ 10.20 (s, 1H), 8.43 (d, 1H), 7.88 (dd, 1H), 7.53 (s, 1H), 7.16 (t, 1H), 6.77 (dd, 1H), 6.43 (d, 1H), 3.48 (s, 3H), 2.33 (s, 3H)

Example 21: Preparation of N'-(5-fluoro-6-methoxypyridine-3-yl)-1-methyl-6-oxo-1,6-dihydropyridine-3-carbohydrazide A title compound (23.1 mg, yield 79%) was obtained in the same manner as in Example 1 except that 5-fluoro-6-methoxy-pyridine-3yl hydrazine hydrochloride was used instead of (2-fluorophenyl)hydrazine.

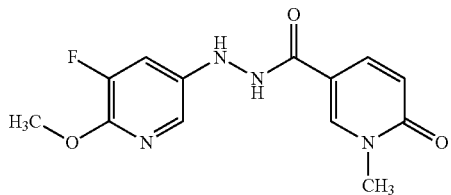 [SMILES: COc1ncc(NNC(=O)c2ccc(=O)n(C)c2)cc1F]

¹H NMR (MeOH-d₄): δ 8.35 (d, 1H), 7.92 (dd, 1H), 7.53 (d, 1H), 7.09 (dd, 1H), 6.55 (d, 1H), 3.89 (s, 3H), 3.60 (s, 3H)

Example 22: Preparation of 4-chloro-N'-(3-fluorophenyl)-1-methyl-6-oxo-1,6-dihydropyridine-3-carbohydrazide A title compound (18.3 mg, yield 62%) was obtained in the same manner as in Example 1 except that 4-chloro-1-methyl-6-oxo-1,6-dihydropyridine-3-carboxylic acid was used instead of 1-methyl-6-oxo-1,6-dihydropyridine-3-carboxylic acid, and (3-fluorophenyl)hydrazine was used instead of (2-fluorophenyl)hydrazine.

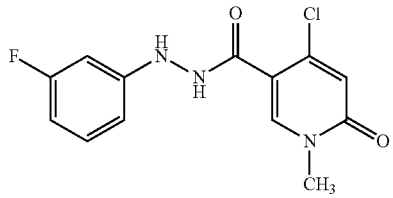 [SMILES: Cn1cc(C(=O)NNc2cccc(F)c2)c(Cl)cc1=O]

$^1$H NMR (MeOH-d$_4$): δ 8.15 (s, 1H), 7.21-7.16 (m, 1H), 6.71-6.69 (m, 2H), 6.63-6.60 (m, 1H), 6.54-6.50 (m, 1H), 3.59 (s, 3H)

Example 23: Preparation of 4-chloro-N'-(4-fluorophenyl)-1-methyl-6-oxo-1,6-dihydropyridine-3-carbohydrazide A title compound (16.0 mg, yield 54%) was obtained in the same manner as in Example 1 except that 4-chloro-1-methyl-6-oxo-1,6-dihydropyridine-3-carboxylic acid was used instead of 1-methyl-6-oxo-1,6-dihydropyridine-3-carboxylic acid, and (4-fluorophenyl)hydrazine was used instead of (2-fluorophenyl)hydrazine.

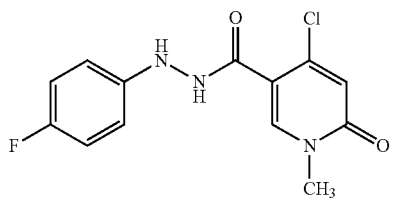 [SMILES: Cn1cc(C(=O)NNc2ccc(F)cc2)c(Cl)cc1=O]

$^1$H NMR (MeOH-d$_4$): δ 8.12 (s, 1H), 6.97-6.93 (m, 2H), 6.91-6.88 (m, 2H), 6.67 (s, 1H), 3.58 (s, 3H)

Example 24: Preparation of 5-chloro-N'-(3-fluorophenyl)-1-methyl-6-oxo-1,6-dihydropyridine-3-carbohydrazide A title compound (18.0 mg, yield 61%) was obtained in the same manner as in Example 1 except that 5-chloro-1-methyl-6-oxo-1,6-dihydropyridine-3-carboxylic acid was used instead of 1-methyl-6-oxo-1,6-dihydropyridine-3-carboxylic acid, and (3-fluorophenyl)hydrazine was used instead of (2-fluorophenyl)hydrazine.

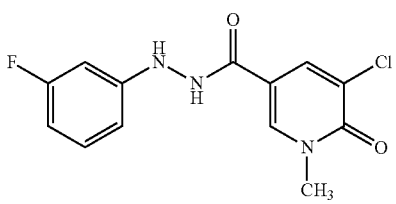 [SMILES: Cn1cc(C(=O)NNc2cccc(F)c2)cc(Cl)c1=O]

$^1$H NMR (DMSO-d$_6$): δ 10.19 (s, 1H), 8.44 (d, 1H), 8.20 (d, 1H), 8.18 (s, 1H), 7.13 (q, 1H), 6.59-6.45 (m, 3H), 3.57 (s, 3H)

Example 25: Preparation of 5-chloro-N'-(4-fluorophenyl)-1-methyl-6-oxo-1,6-dihydropyridine-3-carbohydrazide A title compound (18.6 mg, yield 63%) was obtained in the same manner as in Example 1 except that 5-chloro-1-methyl-6-oxo-1,6-dihydropyridine-3-carboxylic acid was used instead of 1-methyl-6-oxo-1,6-dihydropyridine-3-carboxylic acid, and (4-fluorophenyl)hydrazine was used instead of (2-fluorophenyl)hydrazine.

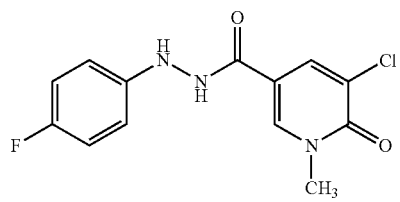

$^1$H NMR (DMSO-d$_6$): δ 10.18 (s, 1H), 8.43 (d, 1H), 8.20 (d, 1H), 7.86 (s, 1H), 6.97 (t, 2H), 6.77-6.75 (m, 2H), 3.56 (s, 3H)

Example 26: Preparation of 5-chloro-N'-(3-chlorophenyl)-1-methyl-6-oxo-1,6-dihydropyridine-3-carbohydrazide A title compound (22.5 mg, yield 72%) was obtained in the same manner as in Example 1 except that 5-chloro-1-methyl-6-oxo-1,6-dihydropyridine-3-carboxylic acid was used instead of 1-methyl-6-oxo-1,6-dihydropyridine-3-carboxylic acid, and (3-chlorophenyl)hydrazine was used instead of (2-fluorophenyl)hydrazine.

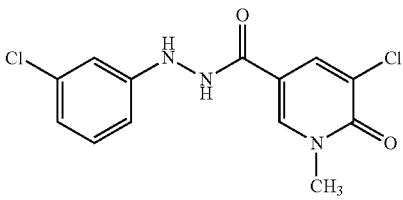 [SMILES: Cn1cc(C(=O)NNc2cccc(Cl)c2)cc(Cl)c1=O]

$^1$H NMR (DMSO-d$_6$): δ 10.20 (s, 1H), 8.45 (d, 1H), 8.21 (d, 1H), 8.18 (s, 1H), 7.14 (t, 1H) 6.74-6.70 (m, 3H), 3.57 (s, 3H)

Example 27: Preparation of 5-chloro-N'-(4-chlorophenyl)-1-methyl-6-oxo-1,6-dihydropyridine-3-carbohydrazide A title compound (19.0 mg, yield 61%) was obtained in the same manner as in Example 1 except that 5-chloro-1-methyl-6-oxo-1,6-dihydropyridine-3-carboxylic acid was used instead of 1-methyl-6-oxo-1,6-dihydropyridine-3-carboxylic acid, and (4-chlorophenyl)hydrazine was used instead of (2-fluorophenyl)hydrazine.

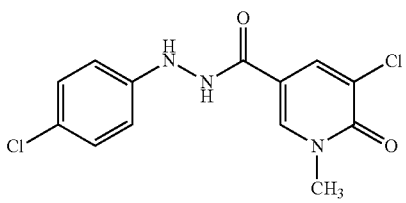 [SMILES: Cn1cc(C(=O)NNc2ccc(Cl)cc2)cc(Cl)c1=O]

$^1$H NMR (DMSO-d$_6$): δ 10.19 (s, 1H), 8.43 (d, 1H), 8.20 (d, 1H), 8.07 (s, 1H), 7.15 (d, 2H), 6.76 (d, 2H), 3.56 (s, 3H)

Example 28: Preparation of 5-chloro-N'-(3-cyanophenyl)-1-methyl-6-oxo-1,6-dihydropyridine-3-carbohydrazide A title compound (23.3 mg, yield 77%) was obtained in the same manner as in Example 1 except that 5-chloro-1-methyl-6-oxo-1,6-dihydropyridine-3-carboxylic acid was used instead of 1-methyl-6-oxo-1,6-dihydropyridine-3-carboxylic acid, and 3-hydrazinylbenzonitrile was used instead of (2-fluorophenyl)hydrazine.

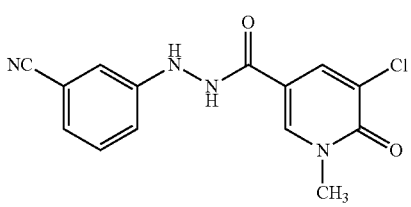 [SMILES: Cn1cc(C(=O)NNc2cccc(C#N)c2)cc(Cl)c1=O]

$^1$H NMR (DMSO-d$_6$): δ10.25 (s, 1H), 8.44 (d, 1H), 8.38 (s, 1H), 8.21 (d, 1H), 7.32 (t, 1H), 7.12-7.07 (m, 3H), 3.57 (s, 3H)

Example 29: Preparation of 5-chloro-N'-(4-cyanophenyl)-1-methyl-6-oxo-1,6-dihydropyridine-3-carbohydrazide A title compound (23.9 mg, yield 79%) was obtained in the same manner as in Example 1 except that 5-chloro-1-methyl-6-oxo-1,6-dihydropyridine-3-carboxylic acid was used instead of 1-methyl-6-oxo-1,6-dihydropyridine-3-carboxylic acid, and 4-hydrazinylbenzonitrile was used instead of (2-fluorophenyl)hydrazine.

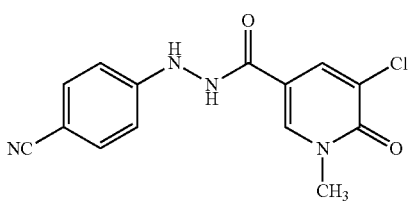 [SMILES: Cn1cc(C(=O)NNc2ccc(C#N)cc2)cc(Cl)c1=O]

$^1$H NMR (DMSO-d$_6$): δ 10.31 (s, 1H), 8.76 (s, 1H), 8.43 (s, 1H), 8.19 (d, 1H), 7.54 (d, 2H), 6.81 (d, 2H), 3.56 (s, 3H)

Example 30: Preparation of 5-chloro-N'-(2,4-difluorophenyl)-1-methyl-6-oxo-1,6-dihydropyridine-3-carbohydrazide A title compound (17.9 mg, yield 57%) was obtained in the same manner as in Example 1 except that 5-chloro-1-methyl-6-oxo-1,6-dihydropyridine-3-carboxylic acid was used instead of 1-methyl-6-oxo-1,6-dihydropyridine-3-carboxylic acid, and (2,4-difluorophenyl)hydrazine was used instead of (2-fluorophenyl)hydrazine.

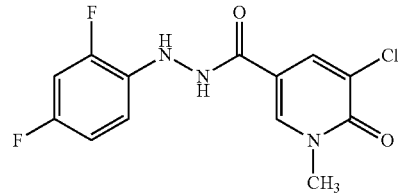 [SMILES: Cn1cc(C(=O)NNc2ccc(F)cc2F)cc(Cl)c1=O]

$^1$H NMR (DMSO-d$_6$) δ 10.22 (s, 1H), 8.42 (d, 1H), 8.19 (d, 1H), 7.75 (s, 1H), 7.15-7.11 (m, 1H), 6.86-6.82 (m, 2H), 3.56 (s, 3H)

Example 31: Preparation of 5-chloro-N'-(3,4-difluorophenyl)-1-methyl-6-oxo-1,6-dihydropyridine-3-carbohydrazide A title compound (16.3 mg, yield 52%) was obtained in the same manner as in Example 1 except that 5-chloro-1-methyl-6-oxo-1,6-dihydropyridine-3-carboxylic acid was used instead of 1-methyl-6-oxo-1,6-dihydropyridine-3-carboxylic acid, and (3,4-difluorophenyl)hydrazine was used instead of (2-fluorophenyl)hydrazine.

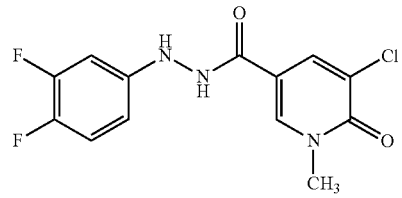

$^1$H NMR (DMSO-d$_6$): δ 10.20 (s, 1H), 8.43 (s, 1H), 8.19 (s, 1H), 8.08 (s, 1H), 7.17 (q, 1H), 6.74-6.55 (m, 2H), 3.56 (s, 3H)

Example 32: Preparation of 5-chloro-N'-(3,5-difluorophenyl)-1-methyl-6-oxo-1,6-dihydropyridine-3-carbohydrazide A title compound (20.1 mg, yield 64%) was obtained in the same manner as in Example 1 except that 5-chloro-1-methyl-6-oxo-1,6-dihydropyridine-3-carboxylic acid was used instead of 1-methyl-6-oxo-1,6-dihydropyridine-3-carboxylic acid, and (3,5-difluorophenyl)hydrazine was used instead of (2-fluorophenyl)hydrazine.

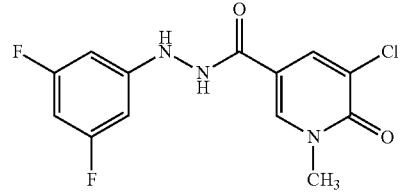 [SMILES: Cn1cc(C(=O)NNc2cc(F)cc(F)c2)cc(Cl)c1=O]

$^1$H NMR (DMSO-d$_6$) δ 10.24 (s, 1H), 8.44 (s, 2H), 8.19 (s, 1H), 6.42-6.38 (m, 3H), 3.56 (s, 3H)

Example 33: Preparation of 7-chloro-N'-(3-fluorophenyl)-5-oxo-1,2,3,5-tetrahydroindolizine-8-carbohydrazide A title compound (24.1 mg, yield 75%) was obtained in the same manner as in Example 1 except that 7-chloro-5-oxo-1,2,3,5-tetrahydroindolizine-8-carboxylic acid was used instead of 1-methyl-6-oxo-1,6-dihydropyridine-3-carboxylic acid, and (3-fluorophenyl)hydrazine was used instead of (2-fluorophenyl)hydrazine.

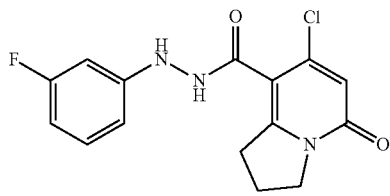 [SMILES: O=C(NNc1cccc(F)c1)c1c(Cl)cc(=O)n2c1CCC2]

$^1$H NMR (MeOH-d$_4$): δ 7.22-7.17 (m, 1H), 6.71-6.69 (m, 1H), 6.63-6.60 (m, 1H), 6.55-6.51 (m, 2H), 4.16 (t, 2H), 3.31 (m, 2H), 2.29 (t, 2H)

Example 34: Preparation of 7-chloro-N'-(4-fluorophenyl)-5-oxo-1,2,3,5-tetrahydroindolizine-8-carbohydrazide A title compound (24.8 mg, yield 77%) was obtained in the same manner as in Example 1 except that 7-chloro-5-oxo-1,2,3,5-tetrahydroindolizine-8-carboxylic acid was used instead of 1-methyl-6-oxo-1,6-dihydropyridine-3-carboxylic acid, and (4-fluorophenyl)hydrazine was used instead of (2-fluorophenyl)hydrazine.

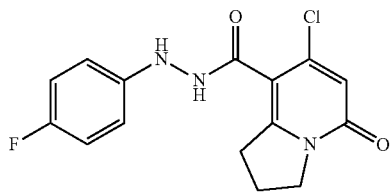 [SMILES: O=C(NNc1ccc(F)cc1)c1c(Cl)cc(=O)n2c1CCC2]

$^1$H NMR (MeOH-d$_4$): δ 6.98-6.95 (m, 2H), 6.92-6.89 (m, 2H), 6.52 (s, 1H), 4.15 (t, 2H), 3.29-3.22 (t, 2H), 2.28 (t, 2H)

Example 35: Preparation of N'-(3-fluorophenyl)-1-methyl-6-oxo-4-((4-(trifluoromethyl)phenyl)amino)-1,6-dihydropyridine-3-carbohydrazide (Step 1) Preparation of 4-chloro-1-methyl-6-oxo-1,6-dihydropyridine-3-carboxylic acid Ethyl 4-chloro-1-methyl-6-oxo-1,6-dihydropyridine-3-carboxylate (300 mg, 1.0 eq) dissolved in a mixed solvent of tetrahydrofuran/methanol (7 mL/7 mL) was added with 2 N sodium hydroxide (4 mL), and stirred at room temperature for 3 hours. Upon completion of the reaction, the resultant was diluted with ethyl acetate and water to separate the aqueous layer. The resulting aqueous layer was acidified with 2 N HCl to form crystals. The resulting crystals were filtered to obtain a title compound (yield; 60%).

(Step 2) Preparation of 1-methyl-6-oxo-4-((4-(trifluoromethyl)phenyl)amino)-1,6-dihydropyridine-3-carboxylic acid 4-chloro-1-methyl-6-oxo-1,6-dihydropyridine-3-carboxylic acid (50 mg, 1.0 eq) prepared in Step 1 was dissolved in tetrahydrofuran (1 mL) and added with 4-(trifluoromethyl)aniline (66 μL, 2.0 eq). The reaction mixture was cooled to 0° C. and dropwisely added with lithium hexamethyldisilazide (500 μL, 3.0 eq). The temperature of the resultant was increased to room temperature and stirred at room temperature for 12 hours. Upon completion of the reaction, the resultant was terminated with an aqueous solution of 1 N HCl, diluted with ethyl acetate, and washed with saturated sodium chloride solution. The resulting organic layer was collected, dried with magnesium sulfate and filtered, concentrated under reduced pressure, and subjected to column chromatography (developing solvent, ethyl acetate:hexane=1:1) to obtain a title compound (yield; 93%).

(Step 3) Preparation of N'-(3-fluorophenyl)-1-methyl-6-oxo-4-((4-(trifluoromethyl)phenyl)amino)-1,6-dihydropyridine-3-carbohydrazide 1-methyl-6-oxo-4-((4-(trifluoromethyl)phenyl)amino)-1,6-dihydropyridine-3-carboxylic acid (31.2 mg, 0.1 mmol) prepared in Step 2 was dissolved in tetrahydrofuran (1 mL), cooled to 0° C., and then sequentially added with 1-ethyl-3-(3-dimethylaminopropyl)carbodiimide (17.1 mg, 0.11 mmol), hydroxybenzotriazole (14.9 mg, 0.11 mmol), and triethylamine (27.9 μL, 0.2 mmol). The resultant was stirred at 0° C. for 30 minutes, added with (3-fluorophenyl)hydrazine (12.6 mg, 0.1 mmol) and dimethylaminopyridine (2.4 mg, 0.02 mmol), and stirred at room temperature for 2 hours. Upon completion of the reaction, the solvent therein was removed, and the resultant was diluted with ethyl acetate and washed with saturated sodium chloride solution. The resulting organic layer was collected, dried with magnesium sulfate and filtered, concentrated under reduced pressure, and subjected to column chromatography (developing solvent, ethyl acetate:hexane=1:2) to obtain a title compound (32.2 mg, yield 79%).

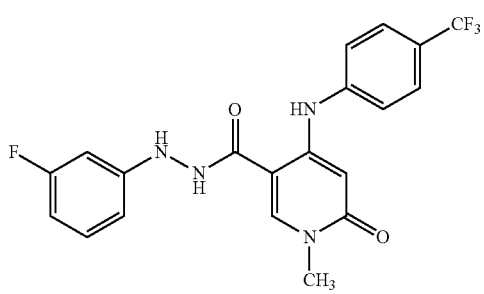 [SMILES: Cn1cc(C(=O)NNc2cccc(F)c2)c(Nc2ccc(C(F)(F)F)cc2)cc1=O]

$^1$H NMR (MeOH-d$_4$): δ 8.31 (s, 1H), 7.67 (d, 2H), 7.41 (d, 2H), 7.19-7.15 (m, 1H), 6.63-6.60 (m, 1H), 6.53-6.51 (m, 1H), 6.51-6.49 (m, 1H), 6.14 (s, 1H), 3.55 (s, 3H)

Example 36: Preparation of N'-(4-fluorophenyl)-1-methyl-6-oxo-4-((4-(trifluoromethyl)phenyl)amino)-1,6-dihydropyridine-3-carbohydrazide A title compound (26.1 mg, yield 62%) was obtained in the same manner as in Example 1 except that (4-fluorophenyl)hydrazine was used instead of (3-fluorophenyl)hydrazine in Step 3 of Example 35.

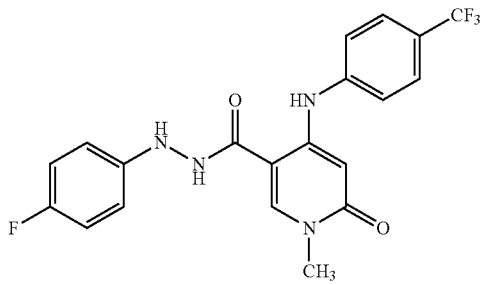 [SMILES: Cn1cc(C(=O)NNc2ccc(F)cc2)c(Nc2ccc(C(F)(F)F)cc2)cc1=O]

¹H NMR (MeOH-d₄): δ 8.29 (s, 1H), 7.67 (d, 2H), 7.41 (d, 2H), 6.97-6.93 (m, 2H), 6.91-6.89 (m, 2H), 6.14 (s, 1H), 3.55 (s, 3H)

Example 37: Preparation of N'-(5-fluoro-6-methoxypyridine-3-yl)-5-(4-fluorophenyl)-1-methyl-6-oxo-1,6-dihydropyridine-3-carbohydrazide (Step 1) Preparation of methyl 5-bromo-1-methyl-6-oxo-1,6-dihydropyridine-3-carboxylate Methyl 5-bromo-6-oxo-1,6-dihydropyridine-3-carboxylate (3.0 g, 1.0 eq) and potassium carbonate (3.6 g, 2.0 eq) were dissolved in N,N-dimethylformamide, and dropwisely added with iodomethane (1.5 eq) at room temperature. The reaction mixture was stirred at 35° C. for 3 hours. Upon completion of the reaction, the resultant was diluted with ethyl acetate, washed with water, dried with magnesium sulfate and filtered, and concentrated under reduced pressure. The resulting residue was dissolved in dichloromethane and crystallized with hexane to obtain a title compound (2.5 g, yield 79%).

(Step 2) Preparation of methyl 5-(4-fluorophenyl)-1-methyl-6-oxo-1,6-dihydropyridine-3-carboxylate Methyl 5-bromo-1-methyl-6-oxo-1,6-dihydropyridine-3-carboxylate (1.5 g, 1.0 eq) prepared in Step 1 was dissolved in N,N-dimethylformamide, sequentially added with (4-fluorophenyl)boronic acid (939 mg, 1.1 eq), tetrakispalladium (705 mg, 0.1 eq), and 2 N sodium carbonate (4.1 ml, 4.0 eq), and allowed to react in a microwave synthesizer maintained at 120° C. for 30 minutes. Upon completion of the reaction, the resultant was terminated by adding with water, and extracted with ethyl acetate. The resulting extract was dried with anhydrous magnesium sulfate, and concentrated under reduced pressure. The resulting residue was purified by column chromatography to obtain a title compound (1.3 g, yield 82%).

(Step 3) Preparation of 5-(4-fluorophenyl)-1-methyl-6-oxo-1,6-dihydropyridine-3-carboxylic acid Methyl 5-(4-fluorophenyl)-1-methyl-6-oxo-1,6-dihydropyridine-3-carboxylate (1.5 g, 1.0 eq) prepared in Step 2 was dissolved in a mixed solvent of tetrahydrofuran/methanol (1:1, 0.1 M), added with 2 N sodium hydroxide (18 ml, 6 eq), and stirred at room temperature for 2 hours. Upon completion of the reaction, the resultant was acidified with an aqueous solution of 1 N HCl, and diluted with ethyl acetate. The resulting organic layer was washed with water, dried and filtered with anhydrous magnesium sulfate, concentrated under reduced pressure to obtain a title compound (1.4 g, yield 99%).

(Step 4) Preparation of N'-(5-fluoro-6-methoxypyridine-3-yl)-5-(4-fluorophenyl)-1-methyl-6-oxo-1,6-dihydropyridine-3-carbohydrazide 5-(4-fluorophenyl)-1-methyl-6-oxo-1,6-dihydropyridine-3-carboxylic acid (24.7 mg, 0.1 mmol) prepared in Step 3 was dissolved in tetrahydrofuran (1 mL), cooled to 0° C., and sequentially added with 1-ethyl-3-(3-dimethylaminopropyl)carbodiimide (17.1 mg, 0.11 mmol), hydroxybenzotriazole (14.9 mg, 0.11 mmol), and triethylamine (27.9 μL, 0.2 mmol). The resultant was stirred at 0° C. for 30 minutes, added with 5-fluoro-6-methoxy-pyridine-3yl hydrazine hydrochloride (12.6 mg, 0.1 mmol) and dimethylaminopyridine (2.4 mg, 0.02 mmol), and stirred at room temperature for 2 hours. Upon completion of the reaction, the solvent therein was removed, and the resultant was diluted with ethyl acetate, and washed with saturated sodium chloride solution. The resulting organic layer was collected, dried with magnesium sulfate and filtered, concentrated under reduced pressure, and subjected to column chromatography (developing solvent, ethyl acetate:hexane=1:1) to obtain a title compound (20.9 mg, yield 54%).

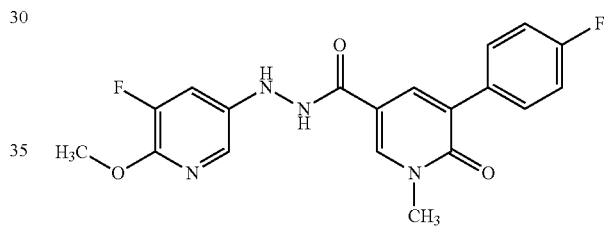

¹H NMR (MeOH-d₄): δ 8.38 (d, 1H), 8.07 (d, 1H), 7.73 (m, 2H), 7.57 (d, 1H), 7.12-7.17 (m, 3H), 3.91 (s, 3H), 3.69 (s, 3H)

Example 38: Preparation of 5-(4-chlorophenyl)-N'-(5-fluoro-6-methoxypyridine-3-yl)-1-methyl-6-oxo-1,6-dihydropyridine-3-carbohydrazide A title compound (24.6 mg, yield 61%) was obtained in the same manner as in Example 37 except that (4-chlorophenyl)boronic acid was used instead of (4-fluorophenyl)boronic acid in Step 2.

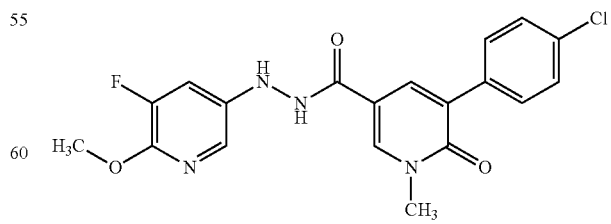

¹H NMR (MeOH-d₄): δ 8.40 (d, 1H), 8.10 (d, 1H), 7.70 (d, 2H), 7.57 (d, 1H), 7.42 (d, 2H), 7.13 (dd, 1H), 3.91 (s, 3H), 3.70 (s, 3H)

Example 39: Preparation of N'-(5-fluoro-6-methoxypyridine-3-yl)-1-methyl-6-oxo-5-(4-(trifluoromethyl)phenyl)-1,6-dihydropyridine-3-carbohydrazide A title compound (27.5 mg, yield 63%) was obtained in the same manner as in Example 37 except that (4-(trifluoromethyl)phenyl)boronic acid was used instead of (4-fluorophenyl)boronic acid in Step 2.

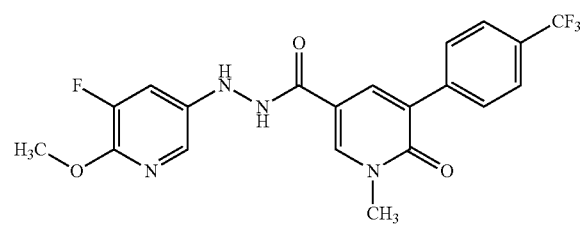 [SMILES: COc1ncc(NNC(=O)c2cc(-c3ccc(C(F)(F)F)cc3)c(=O)n(C)c2)cc1F]

$^1$H NMR (MeOH-d$_4$): δ 8.45 (d, 1H), 8.17 (d, 1H), 7.91 (d, 2H), 7.72 (d, 2H), 7.57 (d, 1H), 7.13 (dd, 1H), 3.91 (s, 3H), 3.69 (s, 3H)

Example 40: Preparation of 5-(4-cyanophenyl)-N'-(5-fluoro-6-methoxypyridine-3-yl)-1-methyl-6-oxo-1,6-dihydropyridine-3-carbohydrazide A title compound (28.3 mg, yield 72%) was obtained in the same manner as in Example 37 except that (4-cyanophenyl)boronic acid was used instead of (4-fluorophenyl)boronic acid in Step 2.

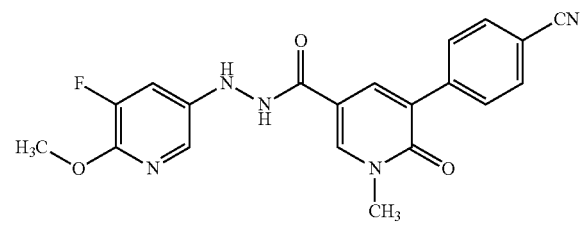 [SMILES: COc1ncc(NNC(=O)c2cc(-c3ccc(C#N)cc3)c(=O)n(C)c2)cc1F]

$^1$H NMR (MeOH-d$_4$): δ 8.46 (d, 1H), 8.18 (d, 1H), 7.92 (d, 2H), 7.79 (d, 2H), 7.75 (d, 1H), 7.12 (dd, 1H), 3.71 (s, 3H), 3.66 (s, 3H)

Example 41: Preparation of N'-(3-fluorophenyl)-1-methyl-6-oxo-5-(pyridine-2-yl)-1,6-dihydropyridine-3-carbohydrazide A title compound (20.6 mg, yield 61%) was obtained in the same manner as in Example 37 except that (2-pyridinyl)boronic acid was used instead of (4-fluorophenyl)boronic acid in Step 2, and (3-fluorophenyl)hydrazine was used instead of 5-fluoro-6-methoxy-pyridine-3yl hydrazine hydrochloride in Step 4.

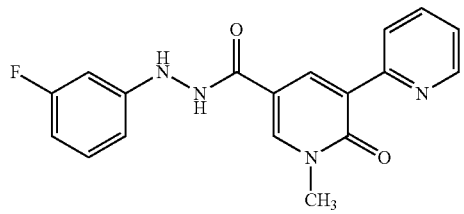 [SMILES: Cn1cc(C(=O)NNc2cccc(F)c2)cc(-c2ccccn2)c1=O]

$^1$H NMR (MeOH-d$_4$): δ 8.67 (d, 1H), 8.63 (d, 1H), 8.49 (d, 1H), 8.27 (d, 1H), 7.89-7.87 (m, 1H), 7.39-7.37 (m, 1H), 7.17-14 (m, 1H), 6.69-6.66 (m, 1H), 6.60-6.58 (m, 1H), 6.52-6.49 (m, 1H), 3.72 (s, 3H)

Example 42: Preparation of 1-(2-fluorophenyl)-N'-(3-fluorophenyl)-6-oxo-1,6-dihydropyridine-3-carbohydrazide A title compound (27.0 mg, yield 79%) was obtained in the same manner as in Example 1 except that 1-(2-fluorophenyl)-6-oxo-1,6-dihydropyridine-3-carboxylic acid was used instead of 1-methyl-6-oxo-1,6-dihydropyridine-3-carboxylic acid, and (3-fluorophenyl)hydrazine was used instead of (2-fluorophenyl)hydrazine.

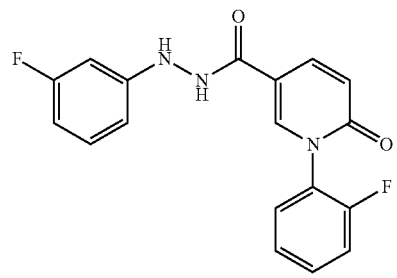 [SMILES: O=C(NNc1cccc(F)c1)c1ccc(=O)n(-c2ccccc2F)c1]

$^1$H NMR (MeOH-d$_4$): δ 8.32 (d, 1H), 8.05 (dd, 1H), 7.65-7.63 (m, 1H), 7.30 (t, 2H), 7.18-7.13 (m, 2H), 7.05-7.01 (m, 2H), 6.56-6.48 (m, 2H)

Example 43: Preparation of N',1-Bis(3-fluorophenyl)-6-oxo-1,6-dihydropyridine-3-carbohydrazide A title compound (21.8 mg, yield 64%) was obtained in the same manner as in Example 1 except that 1-(3-fluorophenyl)-6-oxo-1,6-dihydropyridine-3-carboxylic acid was used instead of 1-methyl-6-oxo-1,6-dihydropyridine-3-carboxylic acid, and (3-fluorophenyl)hydrazine was used instead of (2-fluorophenyl)hydrazine.

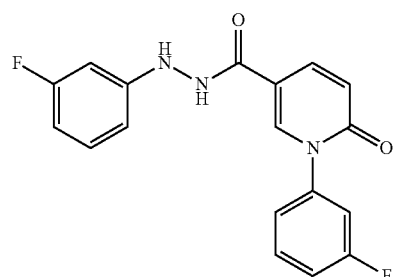

¹H NMR (MeOH-d₄): δ 8.32 (d, 1H), 8.05 (dd, 1H), 7.77-7.75 (m, 1H), 7.42-7.40 (m, 1H), 7.30 (t, 2H), 7.18-7.13 (m, 2H), 6.97-9.64 (m, 1H), 6.56-6.48 (m, 2H)

Example 44: Preparation of N'-(3-fluorophenyl)-1-(4-fluorophenyl)-6-oxo-1,6-dihydropyridine-3-carbohydrazide A title compound (25.6 mg, yield 75%) was obtained in the same manner as in Example 1 except that 1-(4-fluorophenyl)-6-oxo-1,6-dihydropyridine-3-carboxylic acid was used instead of 1-methyl-6-oxo-1,6-dihydropyridine-3-carboxylic acid, and (3-fluorophenyl)hydrazine was used instead of (2-fluorophenyl)hydrazine.

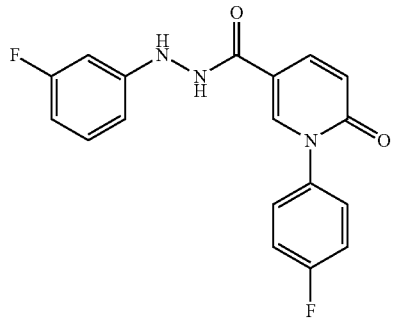 [SMILES: O=C(NNc1cccc(F)c1)c1ccc(=O)n(-c2ccc(F)cc2)c1]

¹H NMR (MeOH-d₄): δ 8.32 (d, 1H), 8.05 (dd, 1H), 7.53-7.50 (m, 2H), 7.30 (t, 2H), 7.18-7.13 (m, 1H), 6.69-6.63 (m, 2H), 6.56-6.48 (m, 2H)

Example 45: Preparation of N'-(4-fluorophenyl)-6-oxo-1-(4-(trifluoromethyl)phenyl)-1,6-dihydropyridine-3-carbohydrazide A title compound (30.1 mg, yield 77%) was obtained in the same manner as in Example 1 except that 6-oxo-1-(4-(trifluoromethyl)phenyl)-1,6-dihydropyridine-3-carboxylic acid was used instead of 1-methyl-6-oxo-1,6-dihydropyridine-3-carboxylic acid, and (4-fluorophenyl)hydrazine was used instead of (2-fluorophenyl)hydrazine.

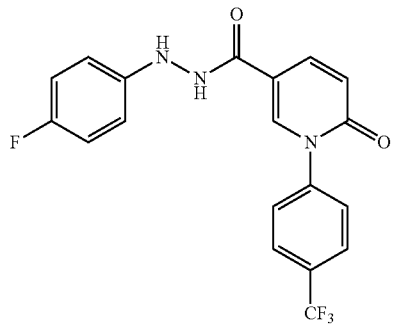 [SMILES: O=C(NNc1ccc(F)cc1)c1ccc(=O)n(-c2ccc(C(F)(F)F)cc2)c1]

¹H NMR (CDCl₃-d): δ 8.16 (d, 1H), 7.80-7.74 (m, 3H), 7.53 (d, 2H), 6.96 (t, 2H), 6.87-6.84 (m, 2H), 6.69 (d, 1H), 6.21 (s, 1H)

Example 46: Preparation of N'-(4-fluorophenyl)-6-oxo-1-(3-(trifluoromethyl)phenyl)-1,6-dihydropyridine-3-carbohydrazide A title compound (30.9 mg, yield 79%) was obtained in the same manner as in Example 1 except that 6-oxo-1-(3-(trifluoromethyl)phenyl)-1,6-dihydropyridine-3-carboxylic acid was used instead of 1-methyl-6-oxo-1,6-dihydropyridine-3-carboxylic acid, and (4-fluorophenyl)hydrazine was used instead of (2-fluorophenyl)hydrazine.

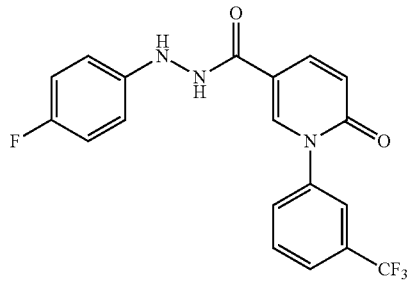 [SMILES: O=C(NNc1ccc(F)cc1)c1ccc(=O)n(-c2cccc(C(F)(F)F)c2)c1]

¹H NMR (CDCl₃-d): δ 8.16 (s, 1H), 7.76-7.60 (m, 6H), 6.98-6.85 (m, 4H), 6.70 (d, 1H), 6.20 (s, 1H)

Example 47: Preparation of 1-(3-chlorophenyl)-N'-(4-fluorophenyl)-6-oxo-1,6-dihydropyridine-3-carbohydrazide A title compound (22.9 mg, yield 64%) was obtained in the same manner as in Example 1 except that 1-(3-chlorophenyl)-6-oxo-1,6-dihydropyridine-3-carboxylic acid was used instead of 1-methyl-6-oxo-1,6-dihydropyridine-3-carboxylic acid, and (4-fluorophenyl)hydrazine was used instead of (2-fluorophenyl)hydrazine.

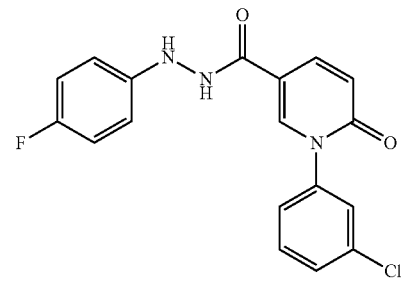 [SMILES: O=C(NNc1ccc(F)cc1)c1ccc(=O)n(-c2cccc(Cl)c2)c1]

¹H NMR (CDCl₃-d): δ 8.12 (d, 1H), 7.75-7.68 (m, 2H), 7.47-7.41 (m, 3H), 7.30-7.26 (m, 1H), 6.96 (t, 2H), 6.88-6.85 (m, 2H), 6.68 (d, 1H), 6.20 (s, 1H)

Example 48: Preparation of 1-(3-chlorophenyl)-N'-(5-fluoro-6-methoxypyridine-3-yl)-6-oxo-1,6-dihydropyridine-3-carbohydrazide A title compound (29.2 mg, yield 75%) was obtained in the same manner as in Example 1 except that 1-(3-chlorophenyl)-6-oxo-1,6-dihydropyridine-3-carboxylic acid was used instead of 1-methyl-6-oxo-1,6-dihydropyridine-3-carboxylic acid, and 5-fluoro-6-methoxy-pyridine-3yl hydrazine hydrochloride was used instead of (2-fluorophenyl) hydrazine.

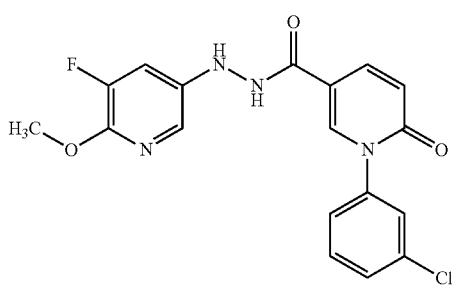 [SMILES: COc1ncc(NNC(=O)c2ccc(=O)n(-c3cccc(Cl)c3)c2)cc1F]

¹H NMR (MeOH-d₄): δ 8.32 (d, 1H), 8.03 (dd, 1H), 7.55-7.60 (m, 4H), 7.44 (m, 1H), 7.12 (dd, 1H), 6.67 (d, 1H), 3.91 (s, 3H)

Example 49: Preparation of N'-(2,4-difluorophenyl)-6-oxo-1-(thiazol-4-ylmethyl)-1,6-dihydropyridine-3-carbohydrazide (Step 1) Preparation of methyl 6-oxo-1,6-dihydropyridine-3-carboxylate 6-oxo-1,6-dihydropyridine-3-carboxylic acid (500 mg, 1.0 eq) was dissolved in methanol (12 mL), cooled to 0° C., and dropwisely added with thionyl chloride (338 μL, 1.2 eq). The temperature of the resultant was increased to 70° C. and stirred under reflux for 6 hours. Upon completion of the reaction, the solvent therein was removed, and the resultant was diluted with ethyl acetate and washed with saturated sodium chloride solution. The resulting organic layer was dried with magnesium sulfate and filtered, concentrated under reduced pressure. The resulting residue was used in next step without purification.

(Step 2) Preparation of methyl 6-oxo-1-(thiazol-4-ylmethyl)-1,6-dihydropyridine-3-carboxylate Methyl 6-oxo-1,6-dihydropyridine-3-carboxylate (100 mg, 1.0 eq) prepared in Step 1 was dissolved in N,N-dimethylformamide (1 mL), added with potassium carbonate (217 mg, 2.4 eq), and stirred at room temperature for 10 minutes. The resultant was dropwisely added with 2-(bromomethyl)thiazole and stirred at room temperature for 5 hours. Upon completion of the reaction, the solvent therein was removed, and the resultant was diluted with ethyl acetate and washed with saturated sodium chloride solution. The resulting organic layer was dried with magnesium sulfate and filtered, concentrated under reduced pressure, and subjected to column chromatography (developing solvent, ethyl acetate:hexane=1:1) to obtain a title compound (yield; 52%).

(Step 3) Preparation of 6-oxo-1-(thiazol-4-ylmethyl)-1,6-dihydropyridine-3-carboxylic acid Methyl 6-oxo-1-(thiazol-4-ylmethyl)-1,6-dihydropyridine-3-carboxylate (88 mg, 1.0 eq) prepared in Step 2 was dissolved in a mixed solvent of tetrahydrofuran/methanol (1.7 mL/1.7 mL), added with 2 N sodium hydroxide (1 mL), and then stirred at room temperature for 3 hours. Upon completion of the reaction, the resultant was diluted with ethyl acetate and water, and the resulting aqueous layer was separated. The thus obtained aqueous layer was acidified with an aqueous solution of 2 N HCl to form crystals, and the thus obtained crystals were filtered to obtain a title compound (yield; 35%).

(Step 4) Preparation of N'-(2,4-difluorophenyl)-6-oxo-1-(thiazol-4-ylmethyl)-1,6-dihydropyridine-3-carbohydrazide 6-oxo-1-(thiazol-4-ylmethyl)-1,6-dihydropyridine-3-carboxylic acid (23.6 mg, 0.1 mmol) prepared in Step 3 was dissolved in tetrahydrofuran (1 mL), cooled to 0° C., and sequentially added with 1-ethyl-3-(3-dimethylaminopropyl) carbodiimide (17.1 mg, 0.11 mmol), hydroxybenzotriazole (14.9 mg, 0.11 mmol), and triethylamine (27.9 μL, 0.2 mmol). The resultant was stirred at 0° C. for 30 minutes, added with (2,4-difluorophenyl)hydrazine (12.6 mg, 0.1 mmol) and dimethylaminopyridine (2.4 mg, 0.02 mmol), and stirred at room temperature for 2 hours. Upon completion of the reaction, the solvent therein was removed, and the resultant was diluted with ethyl acetate and washed with saturated sodium chloride solution. The resulting organic layer was collected, dried with magnesium sulfate and filtered, concentrated under reduced pressure, and subjected to column chromatography (developing solvent, ethyl acetate:hexane=1:2) to obtain a title compound (27.9 mg, yield 77%).

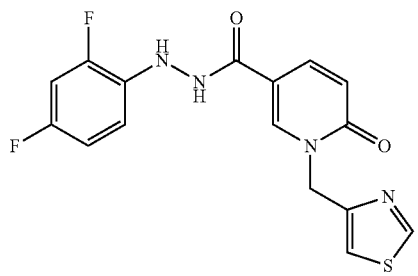 [SMILES: O=C(NNc1ccc(F)cc1F)c1ccc(=O)n(Cc2cscn2)c1]

¹H NMR (MeOH-d₄): δ 8.96 (d, 1H), 8.51 (d, 1H), 7.92 (dd, 1H), 7.59 (s, 1H), 6.93-6.90 (m, 2H), 6.79 (m, 1H), 6.55 (d, 1H), 5.35 (s, 2H)

Example 50: Preparation of N'-(3-fluorophenyl)-6-oxo-1-((6-(trifluoromethyl)pyridin-3-yl)methyl)-1,6-dihydropyridine-3-carbohydrazide A title compound (32.1 mg, yield 79%) was obtained in the same manner as in Example 49 except that 5-(bromomethyl)-2-(trifluoromethyl)pyridine was used instead of 2-(bromomethyl)thiazole in Step 2, and (3-fluorophenyl) hydrazine was used instead of (2,4-difluorophenyl)hydrazine in Step 4.

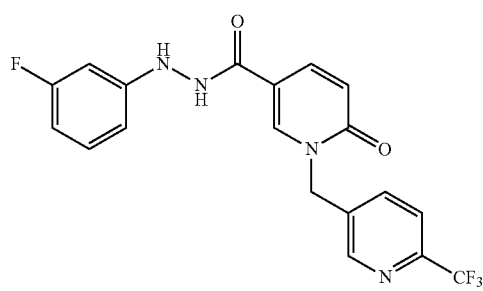 [SMILES: O=C(NNc1cccc(F)c1)c1ccc(=O)n(Cc2ccc(C(F)(F)F)nc2)c1]

¹H NMR (DMSO-d₆): δ 10.21 (s, 1H), 8.81 (s, 1H), 8.67 (d, 1H), 8.19 (s, 1H), 8.01 (d, 1H), 7.99-7.90 (m, 2H), 7.16 (q, 1H), 6.61 (d, 1H), 6.54-6.47 (m, 3H), 5.32 (s, 2H)

Example 51: Preparation of N'-(4-fluorophenyl)-6-oxo-1-((6-(trifluoromethyl)pyridine-3-yl)methyl)-1,6-dihydropyridine-3-carbohydrazide A title compound (21.1 mg, yield 52%) was obtained in the same manner as in Example 49 except that 5-(bromomethyl)-2-(trifluoromethyl)pyridine was used instead of 2-(bromomethyl)thiazole in Step 2, and (4-fluorophenyl)hydrazine was used instead of (2,4-difluorophenyl)hydrazine in Step 4.

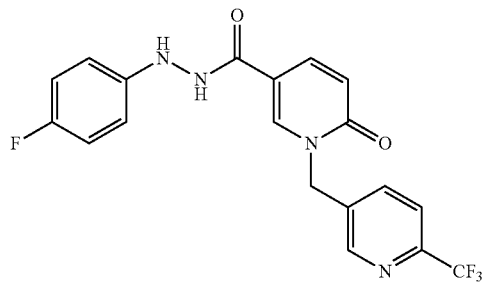 [SMILES: O=C(NNc1ccc(F)cc1)c1ccc(=O)n(Cc2ccc(C(F)(F)F)nc2)c1]

¹H NMR (DMSO-d₆): δ 10.19 (s, 1H), 8.81 (s, 1H), 8.65 (d, 1H), 8.01 (d, 1H), 7.94-7.87 (m, 3H), 6.99 (t, 2H), 6.80-6.78 (m, 2H), 6.50 (d, 1H), 5.31 (s, 2H)

Example 52: Preparation of N'-(3,4-difluorophenyl)-6-oxo-1-((6-(trifluoromethyl)pyridine-3-yl)methyl)-1,6-dihydropyridine-3-carbohydrazide A title compound (27.2 mg, yield 64%) was obtained in the same manner as in Example 49 except that 5-(bromomethyl)-2-(trifluoromethyl)pyridine was used instead of 2-(bromomethyl)thiazole in Step 2, and (3,4-difluorophenyl)hydrazine was used instead of (2,4-difluorophenyl)hydrazine in Step 4.

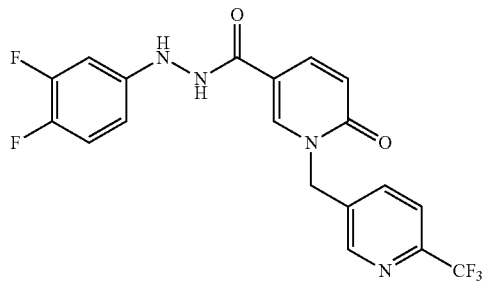 [SMILES: O=C(NNc1ccc(F)c(F)c1)c1ccc(=O)n(Cc2ccc(C(F)(F)F)nc2)c1]

¹H NMR (DMSO-d₆): δ 10.22 (s, 1H), 8.81 (s, 1H), 8.67 (d, 1H), 8.11 (s, 1H), 8.01 (d, 1H), 7.93-7.90 (m, 2H), 7.20 (q, 1H), 6.77-6.73 (m, 1H), 6.59-6.49 (m, 2H), 5.31 (s, 2H)

Example 53: Preparation of N'-(3,5-difluorophenyl)-6-oxo-1-((6-(trifluoromethyl)pyridine-3-yl)methyl)-1,6-dihydropyridine-3-carbohydrazide A title compound (31.8 mg, yield 75%) was obtained in the same manner as in Example 49 except that 5-(bromomethyl)-2-(trifluoromethyl)pyridine was used instead of 2-(bromomethyl)thiazole in Step 2, and (3,5-difluorophenyl)hydrazine was used instead of (2,4-difluorophenyl)hydrazine in Step 4.

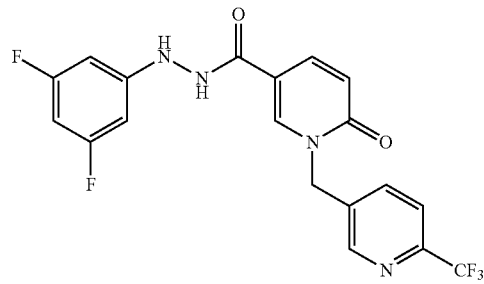 [SMILES: O=C(NNc1cc(F)cc(F)c1)c1ccc(=O)n(Cc2ccc(C(F)(F)F)nc2)c1]

¹H NMR (DMSO-d₆): δ 10.25 (s, 1H), 8.81 (s, 1H), 8.66 (d, 1H), 8.01 (d, 1H), 7.93-7.90 (m, 2H), 7.76 (s, 1H), 7.18-7.14 (m, 1H), 6.88-6.84 (m, 2H), 6.51 (d, 1H), 5.31 (s, 2H)

Example 54: Preparation of N'-(2,4-difluorophenyl)-6-oxo-1-((6-(trifluoromethyl)pyridine-3-yl)methyl)-1,6-dihydropyridine-3-carbohydrazide A title compound (32.7 mg, yield 77%) was obtained in the same manner as in Example 49 except that 5-(bromomethyl)-2-(trifluoromethyl)pyridine was used instead of 2-(bromomethyl)thiazole in Step 2.

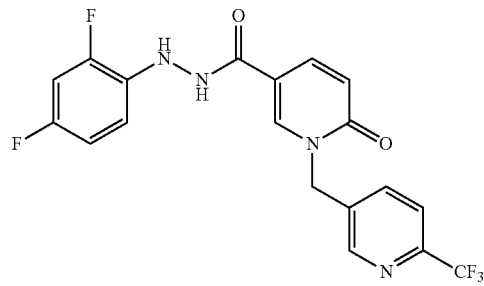 [SMILES: O=C(NNc1ccc(F)cc1F)c1ccc(=O)n(Cc2ccc(C(F)(F)F)nc2)c1]

¹H NMR (DMSO-d₆): δ 10.25 (s, 1H), 8.81 (s, 1H), 8.68 (d, 1H), 8.47 (s, 1H), 8.01 (d, 1H), 7.93-7.90 (m, 2H), 6.52-6.40 (m, 4H), 5.31 (s, 2H)

Example 55: Preparation of N'-(3-fluorophenyl)-6-oxo-1-(2-(4-(4-(trifluoromethyl)phenyl)piperazin-1-yl)ethyl)-1,6-dihydropyridine-3-carbohydrazide A title compound (39.8 mg, yield 79%) was obtained in the same manner as in Example 49 except that 1-(2-chloroethyl)-4-(4-(trifluoromethyl)phenyl)piperazine was used instead of 2-(bromomethyl)thiazole in Step 2, and (3-fluorophenyl)hydrazine was used instead of (2,4-difluorophenyl)hydrazine in Step 4.

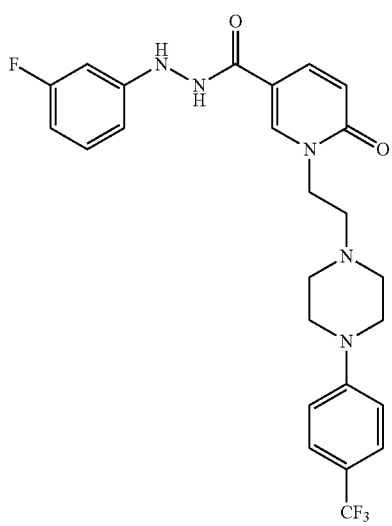 [SMILES: O=C(NNc1cccc(F)c1)c1ccc(=O)n(CCN2CCN(c3ccc(C(F)(F)F)cc3)CC2)c1]

¹H NMR (CDCl₃-d): δ 8.37 (s, 1H), 7.98 (d, 1H), 7.43 (d, 2H), 7.12-7.09 (m, 1H), 6.95 (d, 2H), 6.63-6.58 (m, 2H), 6.54-6.51 (m, 1H) 6.46-6.43 (m, 1H), 4.45-4.43 (m, 2H), 4.37-4.35 (m, 2H), 3.56-3.54 (m, 4H), 3.23-3.16 (m, 4H)

Example 56: Preparation of N'-(4-fluorophenyl)-6-oxo-1-(2-(4-(4-(trifluoromethyl)phenyl)piperazin-1-yl)ethyl)-1,6-dihydropyridine-3-carbohydrazide A title compound (37.8 mg, yield 75%) was obtained in the same manner as in Example 49 except that 1-(2-chloroethyl)-4-(4-(trifluoromethyl)phenyl)piperazine was used instead of 2-(bromomethyl)thiazole in Step 2, and (4-fluorophenyl)hydrazine was used instead of (2,4-difluorophenyl)hydrazine in Step 4.

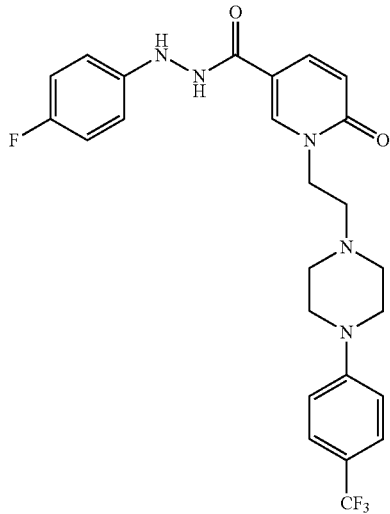 [SMILES: O=C(NNc1ccc(F)cc1)c1ccc(=O)n(CCN2CCN(c3ccc(C(F)(F)F)cc3)CC2)c1]

¹H NMR (CDCl₃-d): δ 8.15 (s, 1H), 7.64 (d, 1H), 7.47 (d, 2H), 6.93 (t, 2H), 6.85-6.81 (m, 4H), 6.61 (d, 1H), 4.44 (t, 2H), 4.29 (t, 2H), 3.59-3.54 (m, 4H), 3.20-3.13 (m, 4H)

Example 57: Preparation of 1-(3-chlorophenethyl)-N'-(3-fluorophenyl)-6-oxo-1,6-dihydropyridine-3-carbohydrazide A title compound (29.7 mg, yield 77%) was obtained in the same manner as in Example 49 except that 1-(2-bromoethyl)-3-chlorobenzene was used instead of 2-(bromomethyl)thiazole in Step 2, and (3-fluorophenyl)hydrazine was used instead of (2,4-difluorophenyl)hydrazine in Step 4.

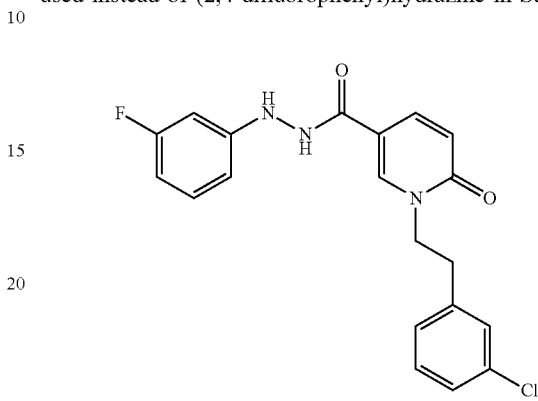

¹H NMR (MeOH-d₄): δ 8.03 (d, 1H), 7.93 (dd, 1H), 7.28-7.21 (m, 3H), 7.18-7.11 (m, 2H), 6.58 (d, 2H), 6.51-6.47 (m, 2H), 4.25 (t, 2H), 3.07 (t, 2H)

Example 58: Preparation of 1-(4-chlorophenethyl)-N'-(3-fluorophenyl)-6-oxo-1,6-dihydropyridine-3-carbohydrazide A title compound (30.5 mg, yield 79%) was obtained in the same manner as in Example 49 except that 1-(2-bromoethyl)-4-chlorobenzene was used instead of 2-(bromomethyl)thiazole in Step 2, and (3-fluorophenyl)hydrazine was used instead of (2,4-difluorophenyl)hydrazine in Step 4.

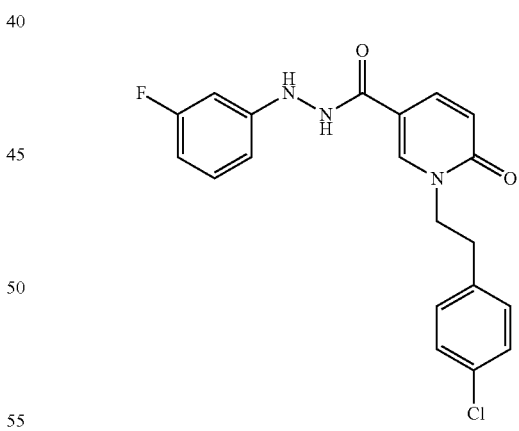

¹H NMR (MeOH-d₄): δ 8.07 (d, 1H), 7.93 (dd, 1H), 7.35-7.25 (m, 3H), 7.02 (t, 2H), 6.80-6.68 (m, 2H), 6.52-6.49 (m, 2H), 4.26 (t, 2H), 3.08 (t, 2H)

Example 59: Preparation of 1-(2-fluorophenethyl)-N'-(3-fluorophenyl)-6-oxo-1,6-dihydropyridine-3-carbohydrazide A title compound (21.1 mg, yield 57%) was obtained in the same manner as in Example 49 except that 1-(2-bromoethyl)-2-fluorobenzene was used instead of 2-(bromomethyl)thiazole in Step 2, and (3-fluorophenyl)hydrazine was used instead of (2,4-difluorophenyl)hydrazine in Step 4.

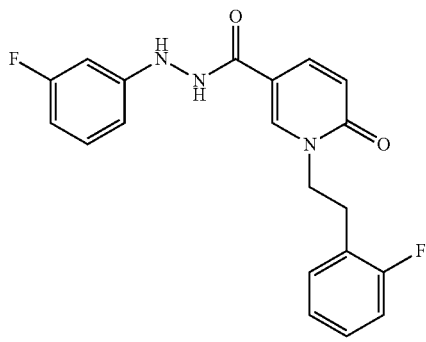 [SMILES: O=C(NNc1cccc(F)c1)c1ccc(=O)n(CCc2ccccc2F)c1]

$^1$H NMR (MeOH-$d_4$): δ 8.07 (d, 1H), 7.93 (dd, 1H), 7.64-7.60 (m, 2H), 7.18-7.10 (m, 3H), 7.07-7.02 (m, 2H), 6.52-6.49 (m, 2H), 4.26 (t, 2H), 3.08 (t, 2H)

Example 60: Preparation of 1-(4-fluorophenethyl)-N'-(3-fluorophenyl)-6-oxo-1,6-dihydropyridine-3-carbohydrazide A title compound (22.9 mg, yield 62%) was obtained in the same manner as in Example 49 except that 1-(2-bromoethyl)-4-fluorobenzene was used instead of 2-(bromomethyl)thiazole in Step 2, and (3-fluorophenyl)hydrazine was used instead of (2,4-difluorophenyl)hydrazine in Step 4.

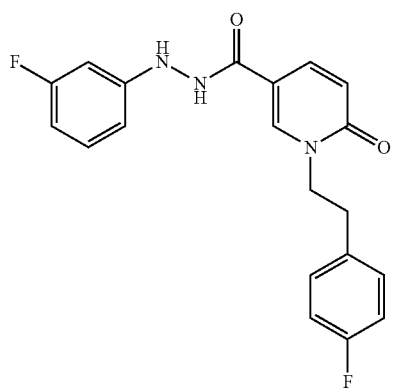 [SMILES: O=C(NNc1cccc(F)c1)c1ccc(=O)n(CCc2ccc(F)cc2)c1]

$^1$H NMR (MeOH-$d_4$): δ 8.07 (d, 1H), 7.93 (dd, 1H), 7.23-7.15 (m, 3H), 7.02 (t, 2H), 6.60-6.58 (m, 2H), 6.52-6.49 (m, 2H), 4.26 (t, 2H), 3.08 (t, 2H)

Example 61: Preparation of 1-(2-(2-fluorophenoxy)ethyl)-N'-(3-fluorophenyl)-6-oxo-1,6-dihydropyridine-3-carbohydrazide A title compound (20.8 mg, yield 54%) was obtained in the same manner as in Example 49 except that 1-(2-bromomethoxy)-2-fluorobenzene was used instead of 2-(bromomethyl)thiazole in Step 2, and (3-fluorophenyl)hydrazine was used instead of (2,4-difluorophenyl)hydrazine in Step 4.

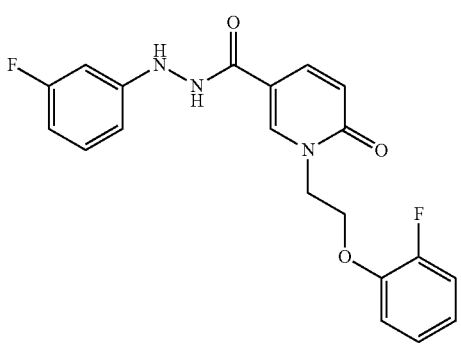 [SMILES: O=C(NNc1cccc(F)c1)c1ccc(=O)n(CCOc2ccccc2F)c1]

$^1$H NMR (MeOH-$d_4$): δ 8.46 (d, 1H), 7.96 (dd, 1H), 7.16 (q, 1H), 7.07-7.04 (m, 3H), 6.92-6.89 (m, 1H), 6.65-6.63 (m, 1H), 6.59-6.53 (m, 2H), 6.51-6.49 (m, 1H), 4.47 (t, 2H), 4.38 (t, 2H)

Example 62: Preparation of 1-(2-(4-chlorophenoxy)ethyl)-N'-(3-fluorophenyl)-6-oxo-1,6-dihydropyridine-3-carbohydrazide A title compound (24.5 mg, yield 61%) was obtained in the same manner as in Example 49 except that 1-(2-bromomethoxy)-4-chlorobenzene was used instead of 2-(bromomethyl)thiazole in Step 2, and (3-fluorophenyl)hydrazine was used instead of (2,4-difluorophenyl)hydrazine in Step 4.

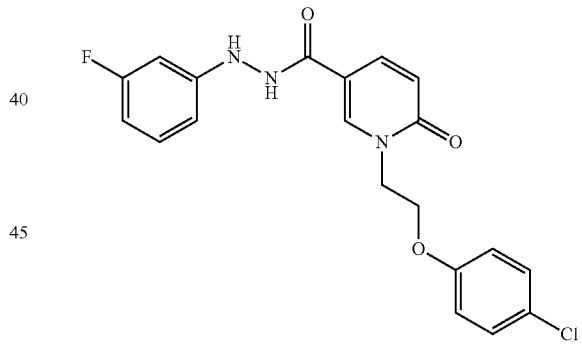

$^1$H NMR (MeOH-$d_4$): δ 8.46 (d, 1H), 7.96 (dd, 1H), 7.35-7.31 (m, 2H), 7.05-7.03 (m, 2H), 6.90-6.88 (m, 1H), 6.65-6.63 (m, 1H), 6.59-6.53 (m, 2H), 6.51-6.49 (m, 1H), 4.47 (t, 2H), 4.38 (t, 2H)

Example 63: Preparation of N'-(3-fluorophenyl)-6-oxo-1-(2-(3-(trifluoromethyl)phenoxy)ethyl)-1,6-dihydropyridine-3-carbohydrazide A title compound (27.4 mg, yield 63%) was obtained in the same manner as in Example 49 except that 1-(2-bromomethoxy)-3-(trifluoromethyl)benzene was used instead of 2-(bromomethyl)thiazole in Step 2, and (3-fluorophenyl)hydrazine was used instead of (2,4-difluorophenyl)hydrazine in Step 4.

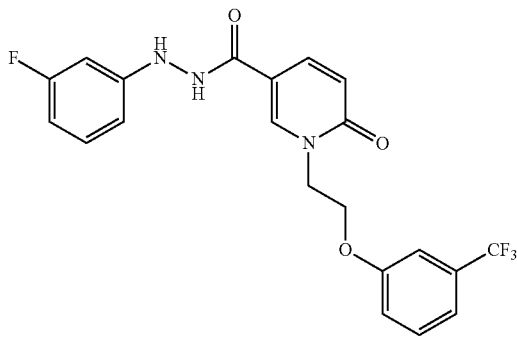 [SMILES: O=C(NNc1cccc(F)c1)c1ccc(=O)n(CCOc2cccc(C(F)(F)F)c2)c1]

¹H NMR (MeOH-d₄): δ 8.43 (d, 1H), 7.95 (dd, 1H), 7.42 (t, 1H), 7.20 (d, 1H), 7.16-7.12 (m, 3H), 6.61 (dd, 1H), 6.61-6.57 (m, 1H), 6.55-6.46 (m, 2H), 4.46 (t, 2H), 4.36 (t, 2H)

Example 64: Preparation of 1-(2-(2,4-dichlorophenoxy)ethyl)-N'-(3-fluorophenyl)-6-oxo-1,6-dihydropyridine-3-carbohydrazide A title compound (31.4 mg, yield 72%) was obtained in the same manner as in Example 49 except that 1-(2-bromomethoxy)-2,4-dichlorobenzene was used instead of 2-(bromomethyl)thiazole in Step 2, and (3-fluorophenyl)hydrazine was used instead of (2,4-difluorophenyl)hydrazine in Step 4.

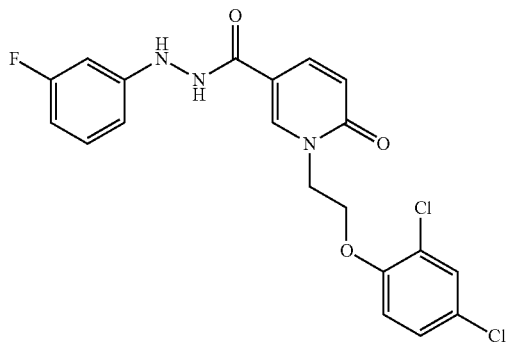 [SMILES: O=C(NNc1cccc(F)c1)c1ccc(=O)n(CCOc2ccc(Cl)cc2Cl)c1]

¹H NMR (MeOH-d₄): δ 8.43 (d, 1H), 7.95 (dd, 1H), 7.42-7.38 (m, 2H), 7.28-7.26 (m, 1H), 7.15-7.12 (m, 2H), 6.61 (dd, 1H), 6.61-6.57 (m, 1H), 6.55-6.46 (m, 2H), 4.46 (t, 2H), 4.36 (t, 2H)

Example 65: Preparation of 1-(2-(4-fluorophenoxy)ethyl)-N'-(3-fluorophenyl)-6-oxo-1,6-dihydropyridine-3-carbohydrazide A title compound (23.5 mg, yield 61%) was obtained in the same manner as in Example 49 except that 1-(2-bromomethoxy)-4-fluorobenzene was used instead of 2-(bromomethyl)thiazole in Step 2, and (3-fluorophenyl)hydrazine was used instead of (2,4-difluorophenyl)hydrazine in Step 4.

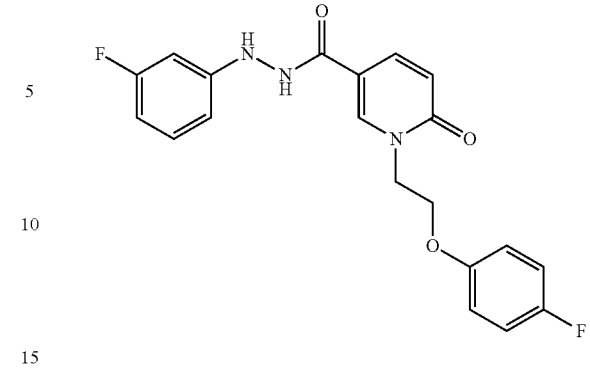

¹H NMR (MeOH-d₄): δ 8.43 (d, 1H), 7.95 (dd, 1H), 7.23-7.19 (m, 2H), 7.15-7.12 (m, 1H), 7.11-7.07 (m, 2H), 6.61 (dd, 1H), 6.61-6.57 (m, 1H), 6.55-6.46 (m, 2H), 4.46 (t, 2H), 4.36 (t, 2H)

Example 66: Preparation of 1-(cyclohexylmethyl)-N'-(3-fluorophenyl)-6-oxo-1,6-dihydropyridine-3-carbohydrazide A title compound (21.3 mg, yield 62%) was obtained in the same manner as in Example 49 except that (bromomethyl)cyclohexane was used instead of 2-(bromomethyl)thiazole in Step 2, and (3-fluorophenyl)hydrazine was used instead of (2,4-difluorophenyl)hydrazine in Step 4.

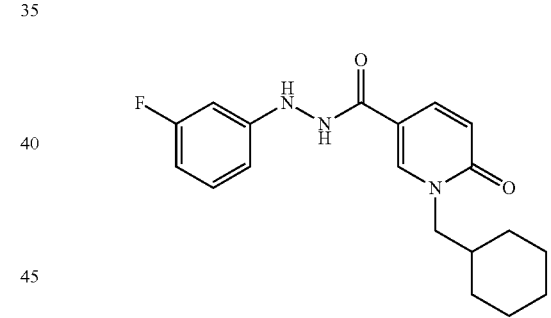

¹H NMR (MeOH-d₄): δ 8.30 (d, 1H), 7.97 (dd, 1H), 7.19-7.15 (m, 1H), 6.65 (dd, 1H), 6.60-6.49 (m, 3H), 3.90 (d, 2H), 1.90-1.86 (d, 1H), 1.78-1.76 (m, 2H), 1.70-1.65 (m, 3H), 1.30-1.21 (m, 3H), 1.10-1.04 (m, 2H)

Example 67: Preparation of 1-(cyclohexylmethyl)-N'-(4-fluorophenyl)-6-oxo-1,6-dihydropyridine-3-carbohydrazide A title compound (18.5 mg, yield 54%) was obtained in the same manner as in Example 49 except that (bromomethyl)cyclohexane was used instead of 2-(bromomethyl)thiazole in Step 2, and (4-fluorophenyl)hydrazine was used instead of (2,4-difluorophenyl)hydrazine in Step 4.

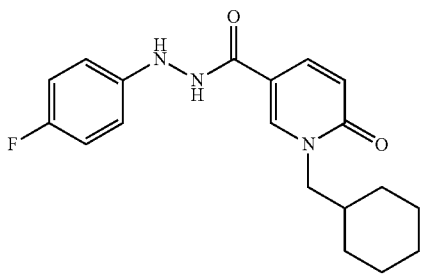 [SMILES: O=C(NNc1ccc(F)cc1)c1ccc(=O)n(CC2CCCCC2)c1]

¹H NMR (MeOH-d₄): δ 8.27 (d, 1H), 7.95 (dd, 1H), 6.95-6.92 (m, 1H), 6.86-6.83 (m, 1H), 6.56 (d, 1H), 3.87 (dd, 2H), 2.99 (s, 1H), 2.86 (s, 1H), 1.89-1.84 (m, 1H), 1.76-1.74 (m, 2H), 1.69-1.63 (m, 3H), 1.29-1.20 (m, 3H), 1.09-1.02 (m, 2H)

Example 68: Preparation of N'-(3-fluorophenyl)-6-oxo-1-(2-oxo-2-(4-(trifluoromethyl)phenyl)ethyl)-1,6-dihydropyridine-3-carbohydrazide A title compound (26.4 mg, yield 61%) was obtained in the same manner as in Example 49 except that 2-bromo-1-(4-(trifluoromethyl)phenyl)ethan-1-one was used instead of 2-(bromomethyl)thiazole in Step 2, and (3-fluorophenyl)hydrazine was used instead of (2,4-difluorophenyl)hydrazine in Step 4.

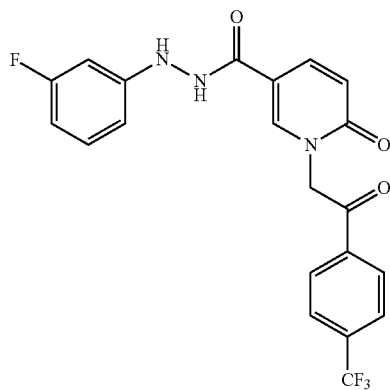 [SMILES: O=C(Cn1cc(C(=O)NNc2cccc(F)c2)ccc1=O)c1ccc(C(F)(F)F)cc1]

¹H NMR (MeOH-d₄): δ 8.34 (d, 1H), 8.25 (d, 2H), 8.04 (d, 1H), 7.88 (d, 2H), 7.17-7.13 (m, 1H), 6.65-6.61 (m, 2H), 6.56-6.53 (m, 1H), 6.50-6.46 (m, 1H), 5.46 (s, 2H)

Example 69: Preparation of N'-(4-fluorophenyl)-6-oxo-1-(2-oxo-2-(4-(trifluoromethyl)phenyl)ethyl)-1,6-dihydropyridine-3-carbohydrazide A title compound (26.9 mg, yield 62%) was obtained in the same manner as in Example 49 except that 2-bromo-1-(4-(trifluoromethyl)phenyl)ethan-1-one was used instead of 2-(bromomethyl)thiazole in Step 2, and (4-fluorophenyl)hydrazine was used instead of (2,4-difluorophenyl)hydrazine in Step 4.

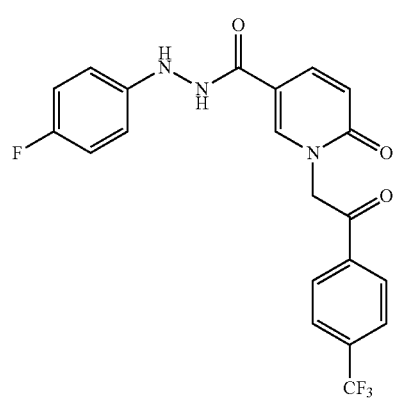 [SMILES: O=C(Cn1cc(C(=O)NNc2ccc(F)cc2)ccc1=O)c1ccc(C(F)(F)F)cc1]

¹H NMR (MeOH-d₄): δ 8.34 (d, 1H), 8.25 (d, 2H), 8.04 (d, 1H), 7.88 (d, 2H), 7.05-7.03 (m, 2H), 6.91-6.87 (m, 2H), 6.50-6.46 (m, 1H), 5.46 (s, 2H)

Example 70: Preparation of N'-(3,4-difluorophenyl)-6-oxo-1-(2-oxo-2-(4-(trifluoromethyl)phenyl)ethyl)-1,6-dihydropyridine-3-carbohydrazide A title compound (24.4 mg, yield 54%) was obtained in the same manner as in Example 49 except that 2-bromo-1-(4-(trifluoromethyl)phenyl)ethan-1-one was used instead of 2-(bromomethyl)thiazole in Step 2, and (3,4-difluorophenyl)hydrazine was used instead of (2,4-difluorophenyl)hydrazine in Step 4.

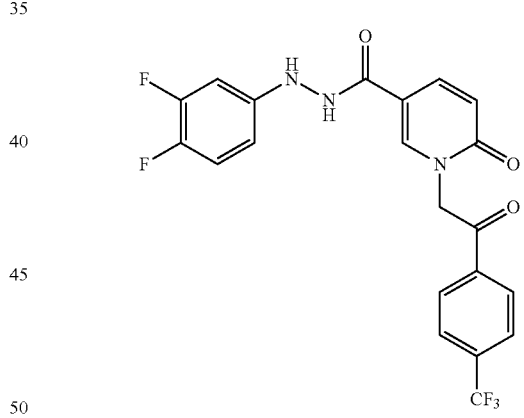

¹H NMR (MeOH-d₄): δ 8.34 (d, 1H), 8.25 (d, 2H), 8.04 (d, 1H), 7.88 (d, 2H), 7.42-7.40 (m, 1H), 6.98-6.95 (m, 2H), 6.50-6.46 (m, 2H), 5.46 (s, 2H)

Example 71: Preparation of 2-(5-(2-(3-fluorophenyl)hydrazinecarbonyl)-2-oxopyridine-1(2H)-yl)-N-(4-(trifluoromethyl)phenyl)acetamide A title compound (27.4 mg, yield 61%) was obtained in the same manner as in Example 49 except that 2-bromo-N-(4-(trifluoromethyl)phenyl)acetamide was used instead of 2-(bromomethyl)thiazole in Step 2, and (3-fluorophenyl)hydrazine was used instead of (2,4-difluorophenyl)hydrazine in Step 4.

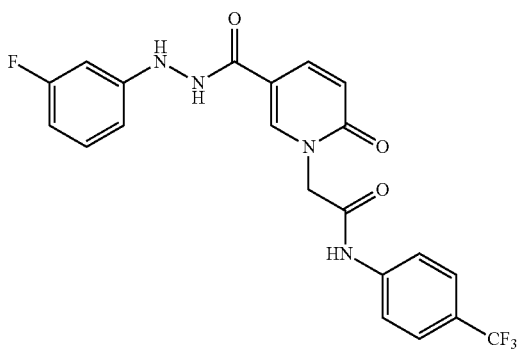 [SMILES: O=C(Cn1cc(C(=O)NNc2cccc(F)c2)ccc1=O)Nc1ccc(C(F)(F)F)cc1]

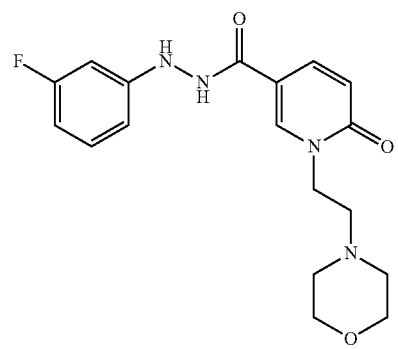

¹H NMR (MeOH-d₄): δ 8.40 (d, 1H), 8.02 (dd, 1H), 7.78 (d, 2H), 7.61 (d, 2H), 7.16-7.15 (m, 1H), 6.66-6.48 (m, 4H), 4.92 (s, 2H)

Example 72: Preparation of 2-(5-(2-(4-fluorophenyl)hydrazinecarbonyl)-2-oxopyridine-1(2H)-yl)-N-(4-(trifluoromethyl)phenyl)acetamide A title compound (28.2 mg, yield 63%) was obtained in the same manner as in Example 49 except that 2-bromo-N-(4-(trifluoromethyl)phenyl)acetamide was used instead of 2-(bromomethyl)thiazole in Step 2, and (4-fluorophenyl)hydrazine was used instead of (2,4-difluorophenyl)hydrazine in Step 4.

¹H NMR (MeOH-d₄): δ 8.36 (d, 1H), 7.97 (d, 1H), 7.19-7.14 (m, 1H), 6.65 (d, 1H), 6.58-6.49 (m, 3H), 4.18 (t, 2H), 3.66 (m, 4H), 2.71 (t, 2H), 2.53 (m, 4H)

Example 74: Preparation of N'-(4-fluorophenyl)-1-(2-morpholinoethyl)-6-oxo-1,6-dihydropyridine-3-carbohydrazide A title compound (22.0 mg, yield 61%) was obtained in the same manner as in Example 1 except that 1-(2-morpholinoethyl)-6-oxo-1,6-dihydropyridine-3-carboxylic acid was used instead of 1-methyl-6-oxo-1,6-dihydropyridine-3-carboxylic acid, and (4-fluorophenyl)hydrazine was used instead of (2-fluorophenyl)hydrazine.

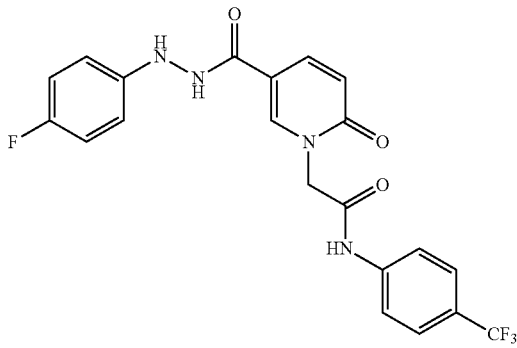 [SMILES: O=C(Cn1cc(C(=O)NNc2ccc(F)cc2)ccc1=O)Nc1ccc(C(F)(F)F)cc1]

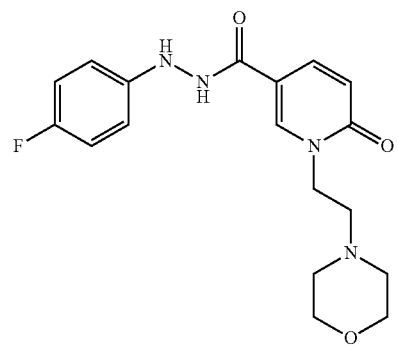 [SMILES: O=C(NNc1ccc(F)cc1)c1ccc(=O)n(CCN2CCOCC2)c1]

¹H NMR (MeOH-d₄): δ 8.37 (d, 1H), 8.01 (dd, 1H), 7.77 (d, 2H), 7.61 (d, 2H), 6.95-6.91 (m, 2H), 6.87-6.84 (m, 2H), 6.60 (d, 1H), 4.92 (d, 2H)

Example 73: Preparation of N'-(3-fluorophenyl)-1-(2-morpholinoethyl)-6-oxo-1,6-dihydropyridine-3-carbohydrazide A title compound (25.9 mg, yield 72%) was obtained in the same manner as in Example 1 except that 1-(2-morpholinoethyl)-6-oxo-1,6-dihydropyridine-3-carboxylic acid was used instead of 1-methyl-6-oxo-1,6-dihydropyridine-3-carboxylic acid, and (3-fluorophenyl)hydrazine was used instead of (2-fluorophenyl)hydrazine.

¹H NMR (MeOH-d₄): δ 8.33 (d, 1H), 7.93 (dd, 1H), 6.94-6.84 (m, 2H), 6.84-6.82 (m, 2H), 6.54 (d, 1H), 4.16 (t, 2H), 3.64 (m, 4H), 2.69 (t, 2H), 2.51 (m, 4H)

Example 75: Preparation of 2-(5-(2-(3-fluorophenyl)hydrazine-1-carbonyl)-2-oxopyridine-1(2H)-yl)-N,N-dimethylacetamide A title compound (22.9 mg, yield 69%) was obtained in the same manner as in Example 1 except that 1-(2-(dimethylamino)-2-oxoethyl)-6-oxo-1,6-dihydropyridine-3-carboxylic acid was used instead of 1-methyl-6-oxo-1,6-dihydropyridine-3-carboxylic acid, and (3-fluorophenyl)hydrazine was used instead of (2-fluorophenyl)hydrazine.

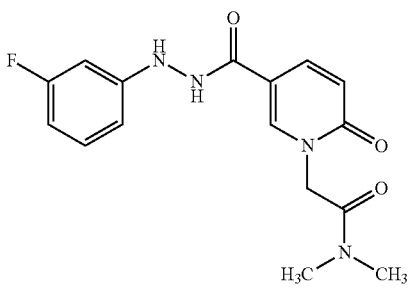 [SMILES: CN(C)C(=O)Cn1cc(C(=O)NNc2cccc(F)c2)ccc1=O]

¹H NMR (MeOH-d₄): δ 8.28 (d, 1H), 8.00 (d, 1H), 7.18-7.14 (m, 1H), 6.66-6.48 (m, 4H), 4.97 (s, 2H), 3.17 (s, 3H), 2.99 (s, 3H)

Example 76: Preparation of N'-(3-fluorophenyl)-1-(2-methoxyethyl)-6-oxo-1,6-dihydropyridine-3-carbohydrazide A title compound (17.4 mg, yield 57%) was obtained in the same manner as in Example 1 except that 1-(2-methoxyethyl)-6-oxo-1,6-dihydropyridine-3-carboxylic acid was used instead of 1-methyl-6-oxo-1,6-dihydropyridine-3-carboxylic acid, and (3-fluorophenyl)hydrazine was used instead of (2-fluorophenyl)hydrazine.

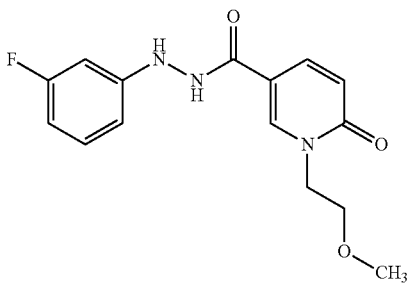 [SMILES: COCCn1cc(C(=O)NNc2cccc(F)c2)ccc1=O]

¹H NMR (MeOH-d₄): δ 8.29 (s, 1H), 7.93 (dd, 1H), 7.13 (dd, 1H), 6.62-6.60 (m, 1H), 6.55-6.45 (m, 3H), 4.20 (t, 2H), 3.65 (t, 2H), 3.30 (s, 3H)

Example 77: Preparation of 2-(5-(2-(4-fluorophenyl)hydrazinecarbonyl)-2-oxopyridine-1(2H)-yl)-N,N-dimethylacetamide A title compound (17.3 mg, yield 52%) was obtained in the same manner as in Example 1 except that 1-(2-(dimethylamino)-2-oxoethyl)-6-oxo-1,6-dihydropyridine-3-carboxylic acid was used instead of 1-methyl-6-oxo-1,6-dihydropyridine-3-carboxylic acid, and (4-fluorophenyl)hydrazine was used instead of (2-fluorophenyl)hydrazine.

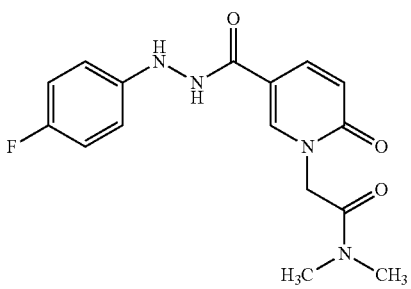 [SMILES: CN(C)C(=O)Cn1cc(C(=O)NNc2ccc(F)cc2)ccc1=O]

¹H NMR (MeOH-d₄): δ 8.28 (d, 1H), 8.00 (d, 1H), 7.12-7.10 (m, 2H), 6.90-6.85 (m, 2H), 6.56-6.48 (m, 1H), 4.97 (s, 2H), 3.17 (s, 3H), 2.99 (s, 3H)

Example 78: Preparation of N'-(4-fluorophenyl)-1-(2-methoxyethyl)-6-oxo-1,6-dihydropyridine-3-carbohydrazide A title compound (19.8 mg, yield 65%) was obtained in the same manner as in Example 1 except that 1-(2-methoxyethyl)-6-oxo-1,6-dihydropyridine-3-carboxylic acid was used instead of 1-methyl-6-oxo-1,6-dihydropyridine-3-carboxylic acid, and (4-fluorophenyl)hydrazine was used instead of (2-fluorophenyl)hydrazine.

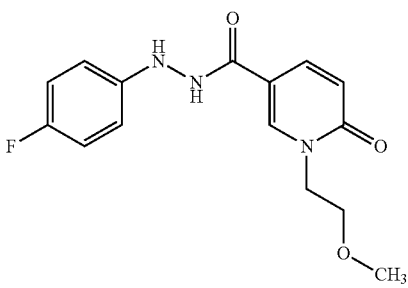 [SMILES: COCCn1cc(C(=O)NNc2ccc(F)cc2)ccc1=O]

¹H NMR (MeOH-d₄): δ 8.29 (s, 1H), 7.07-7.02 (m, 2H), 6.92-6.88 (m, 2H), 6.55-6.45 (m, 2H), 4.20 (t, 2H), 3.65 (t, 2H), 3.30 (s, 3H)

Example 79: Preparation of (1⁵E,10E)-5⁵-fluoro-1¹,1²-dihydro-7-oxa-3,4-diaza-1(5,1)-pyridina-5(1,2)-benzenacyclododecaphan-10-ene-1²,2,6-trione (Step 1): Preparation of methyl 1-allyl-6-oxo-1,6-dihydropyridine-3-carboxylate Methyl 6-oxo-1,6-dihydropyridine-3-carboxylate (100 mg, 0.652 mmol) was dissolved in N,N-dimethylformamide (1.5 mL) and added with potassium carbonate (216 mg, 2.4 eq). The resultant was stirred for about 20 minutes, added with allyl bromide (0.067 mL, 1.2 eq) and sodium iodide (48.8 mg, 0.5 eq), and stirred for 2 hours. Upon completion of the reaction, the resultant was added with ethyl acetate and water, and then extracted an organic layer. The organic layer was dried with magnesium sulfate and filtered. The resulting filtrate was concentrated and purified by column (hexane:ethyl acetate=2:1) to obtain a title compound (120 mg, yield 95%).

(Step 2): Preparation of 1-allyl-6-oxo-1,6-dihydropyridine-3-carboxylic acid

Methyl 1-allyl-6-oxo-1,6-dihydropyridine-3-carboxylate (800 mg, 4.14 mmol) prepared in Step 1 was dissolved in methanol (50 mL) and added with 1 N sodium hydroxide (12.4 mL, 3.0 eq), and stirred at room temperature for 12 hours. Upon completion of the reaction, the reaction solvent was removed, and the resultant was diluted with water, and adjusted to pH 6 by adding an aqueous solution of 3 N HCl. The resulting precipitate was filtered and dried under reduced pressure to obtain a title compound (654 mg, yield 88%).

(Step 3) Preparation of but-3-en-1-yl 2-nitrobenzoate

2-Nitrobenzoic acid (1 g, 5.98 mmol), 1-ethyl-3-(3-dimethylaminopropyl)carbodiimide (1.71 g, 1.5 eq), and dimethylaminopyridine (365 mg, 0.5 eq) were dissolved in dichloromethane (30 mL). The resultant was stirred for about 20 minutes, added with butenol (0.617 mL, 1.2 eq) and allowed to react at room temperature for 12 hours. Upon completion of the reaction, the reaction mixture was washed with water, saturated sodium bicarbonate solution, and saturated sodium chloride solution, and the resulting organic layer was dried with magnesium sulfate and filtered. The resulting filtrate was concentrated and purified by column (hexane:ethyl acetate=20:1→9:1) to obtain a title compound (800 mg, yield 60%).

(Step 4) Preparation of but-3-en-1-yl 2-aminobenzoate

But-3-en-1-yl 2-nitrobenzoate (500 mg, 2.26 mmol) prepared in Step 3 was dissolved in ethyl acetate (20 mL), added with tin(II) chloride dihydrate (1.53 g, 3 eq), and stirred at 50° C. for 12 hours. Upon completion of the reaction, the temperature of the resultant was cooled to room temperature, and extracted by adding 10% sodium bicarbonate solution and ethyl acetate. The resulting aqueous layer was additionally extracted twice. The resulting organic layer was dried and filtered. The resulting filtrate was concentrated and purified by column (hexane:ethyl acetate=20:1→9:1) to obtain a title compound (300 mg, yield 69%).

(Step 5) Preparation of but-3-en-1-yl 2-hydrazinylbenzoate hydrochloride

But-3-en-1-yl 2-aminobenzoate (220 mg, 1.15 mmol) prepared in Step 4 was dispersed in conc. HCl (2 mL) and slowly added with sodium nitrate (83 mg, 1.05 eq) dissolved in 1 mL of water at 0° C. The resultant was stirred for about 1 hour, slowly added with tin(II) chloride dihydrate (520 mg, 2.0 eq) dissolved in conc. HCl (1 mL) at 0° C., and stirred at room temperature for 1 hour. The resulting solid was filtered, washed with hexane/dimethyl ether, etc., and dried under reduced pressure to obtain a title compound (210 mg, yield 75%).

(Step 6) Preparation of but-3-en-1-yl 2-(2-(1-allyl-6-oxo-1,6-dihydropyridine-3-carbonyl)hydrazinyl)benzoate 1-allyl-6-oxo-1,6-dihydropyridine-3-carboxylic acid (200 mg, 0.558 mmol) prepared in Step 5, 1-ethyl-3-(3-dimethylaminopropyl)carbodiimide (320 mg, 1.5 eq), hydroxybenzotriazole (225 mg, 1.5 eq), dimethylaminopyridine (68 mg, 0.5 eq), and diisopropylethylamine (0.62 mL, 3.0 eq) were dissolved in tetrahydrofuran/N,N-dimethylformamide (5 mL, 5 mL). The resultant was stirred for 2 hours, added with but-3-en-1-yl 2-hydrazinylbenzoate hydrochloride (406 mg, 1.5 eq) prepared in Step 2, and allowed to react for 12 hours. Upon completion of the reaction, the resultant was added with ethyl acetate and water, and extracted an organic layer. The resulting organic layer was dried with magnesium sulfate and filtered. The resulting filtrate was purified by column (hexane:ethyl acetate=1:1→1:2) to obtain a title compound (290 mg, yield 70%).

(Step 7): Preparation of $(1^5E,10E)$-$5^5$-fluoro-$1^1$,$1^2$-dihydro-7-oxa-3,4-diaza-1(5,1)-pyridina-5(1,2)-benzenacyclododecaphan-10-ene-$1^2$,2,6-trione But-3-en-1-yl 2-(2-(1-allyl-6-oxo-1,6-dihydropyridine-3-carbonyl)hydrazinyl)benzoate (280 mg, 0.762 mmol) prepared in Step 6 was dissolved in dichloromethane (20 mL), added with Grubbs catalyst (65 mm, 0.1 eq), and allowed to react at 50° C. for 12 hours. Upon completion of the reaction, the solvent in the reaction mixture was removed and the resultant was purified by column (dichloromethane:methanol=30:1→20:1) to obtain a title compound (27 mg, yield 10%).

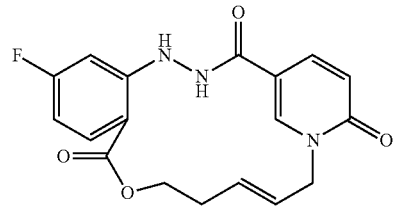 [SMILES: O=C1NNc2cc(F)ccc2C(=O)OCC/C=C/Cn2cc1ccc2=O]

$^1$H NMR (MeOH-$d_4$): δ 8.18 (d, 1H), 7.81-7.74 (m, 2H), 6.69-6.67 (m, 1H), 6.45-6.40 (m, 1H), 6.35 (d, 1H), 5.83-5.71 (m, 2H), 4.69-4.53 (m, 2H), 4.50-4.45 (m, 2H), 2.55-2.52 (m, 2H)

Example 80: Preparation of $(1^5E,9E)$-$1^1$,$1^2$-dihydro-7-oxa-3,4-diaza-1(5,1)-pyridina-5(1,2)-benzenacycloundecaphan-9-ene-$1^2$,2,6-trione A title compound (15 mg, yield 11%) was obtained in the same manner as in Example 79 except that 4-fluoro-2-nitrobenzoic acid was used instead of 2-nitrobenzoic acid.

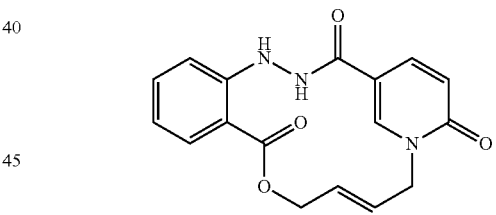

$^1$H NMR (MeOH-$d_4$): δ7.97 (d, 1H), 7.76 (d, 1H), 7.63 (dd, 1H), 7.38 (q, 1H), 6.94 (d, 1H), 6.73 (t, 1H), 6.29 (d, 1H), 5.75 (m, 1H), 5.64 (m, 1H), 4.48 (m, 4H), 2.52 (m, 2H)

Example 81: Preparation of $(1^5E,9E)$-$1^1$,$1^2$-dihydro-6-oxa-3,4-diaza-1(5,1)-pyridina-5(1,2)-benzenacycloundecaphan-9-ene-$1^2$,2-dione

(Step 1) Preparation of 1-(but-3-en-1-yloxy)-2-nitrobenzene 2-nitrophenol (600 mg, 4.31 mmol) was dissolved in N,N-dimethylformamide (10 mL) and added with $Cs_2CO_3$ (7.03 g, 5 eq). The resultant was stirred for about 20 minutes, added with bromobutene (0.87 mL, 2.0 eq) and then stirred at room temperature for 12 hours. Upon completion of the reaction, the resultant was added with ethyl acetate and water, and extracted an organic layer. The organic layer was dried with magnesium sulfate and filtered. The resulting filtrate was concentrated and purified by column (hexane:ethyl acetate=9:1) to obtain a title compound (810 mg, yield 97%).

(Step 2) Preparation of 2-(but-3-en-1-yloxy)aniline 1-(but-3-en-1-yloxy)-2-nitrobenzene (400 mg, 2.07 mmol) prepared in Step 1 was dissolved in a mixed solvent of ethanol/water (8 mL/2 mL) and added with Fe (1.15 g, 10 eq) and ammonium chloride (55 mg, 0.5 eq), and stirred at 80° C. for 2 hours. Upon completion of the reaction, the temperature of the resultant was cooled to room temperature and filtered. The solvent of the reaction mixture was removed and purified by column (hexane:ethyl acetate=9:1) to obtain a title compound (328 mg, yield 97%).

(Step 3) Preparation of (2-(but-3-en-1-yloxy)phenyl)hydrazine hydrochloride 2-(But-3-en-1-yloxy)aniline (330 mg, 2.02 mmol) prepared in Step 2 was dissolved in an aqueous solution of 6 M HCl (6 mL) at 0° C., and slowly added with sodium nitrite (NaNO$_2$) (223 mg, 1.6 eq) dissolved in 3 mL of water. The resultant was stirred at 0° C. for about 60 minutes, slowly added with tin(II) chloride dihydrate (1.36 g, 3.0 eq) dissolved in an aqueous solution of 6 M HCl (9 mL), and stirred for 2 hours. Upon completion of the reaction, the reaction mixture was alkalinized by adding with 50% sodium hydroxide (NaOH) solution, and extracted with dimethyl ether. The resulting organic layer was dried with magnesium sulfate and filtered. The resultant was solidified by adding with an aqueous solution of 2 M HCl/dimethyl ether to form hydrochloride. The resultant was filtered and dried under reduced pressure to obtain a title compound (127 mg, yield 27%).

(Step 4) Preparation of 1-allyl-N'-(2-(but-3-en-1-yloxy)phenyl)-6-oxo-1,6-dihydropyridine-3-carbohydrazide 1-Allyl-6-oxo-1,6-dihydropyridine-3-carboxylic acid (100 mg, 0.558 mmol) prepared in Step 5 of Example 79, 1-ethyl-3-(3-dimethylaminopropyl)carbodiimide (160 mg, 1.5 eq), hydroxybenzotriazole (113 mg, 1.5 eq), dimethylaminopyridine (34 mg, 0.5 eq), and diisopropylethylamine (0.31 mL, 3.0 eq) were dissolved in tetrahydrofuran/N,N-dimethylformamide (3 mL/3 mL). The resultant was stirred for 2 hours, added with (2-(but-3-en-1-yloxy)phenyl)hydrazine hydrochloride (127 mg, 0.558 mmol) prepared in Step 3, and allowed to react for 12 hours. Upon completion of the reaction, the resultant was added with ethyl acetate and water, and extracted an organic layer. The organic layer was dried with magnesium sulfate and filtered. The resulting filtrate was concentrated and purified by column (hexane:ethyl acetate=1:1→1:2) to obtain a title compound (28 mg, yield 15%).

(Step 5) Preparation of (1$^5$E,9E)-1$^1$,1$^2$-dihydro-6-oxa-3,4-diaza-1(5,1)-pyridina-5(1,2)-benzenacycloundecaphan-9-ene-1$^2$,2-dione 1-Allyl-N'-(2-(but-3-en-1-yloxy)phenyl)-6-oxo-1,6-dihydropyridine-3-carbohydrazide (28 mg, 0.0825 mmol) prepared in Step 4 was dissolved in dichloromethane (40 mL), added with Grubbs catalyst (11.2 mg, 0.16 eq), and allowed to react at 50° C. for 12 hours. Upon completion of the reaction, the solvent of the reaction mixture was removed and purified by column (dichloromethane:methanol=30:1) to obtain a title compound (14 mg, yield 55%).

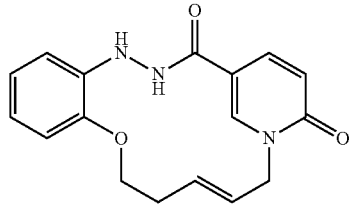 [SMILES: O=C1NNc2ccccc2OCC/C=C/Cn2cc1ccc2=O]

$^1$H NMR (CDCl$_3$-d): δ 9.40 (s, 1H), 8.01 (d, 1H), 6.97-6.85 (m, 3H), 6.53 (d, 1H), 6.09 (s, 1H), 5.83 (m, 1H), 5.35 (m, 1H), 4.49 (d, 2H), 4.40 (d, 2H), 2.62 (m, 2H)

Formulation Example 1: Tablets 50 mg of the compounds prepared in Example 1 and 20 mg of magnesium stearate were granulated into 35 mg of soluble starch and dried, and then mixed with 65 mg of lactose and 30 mg of corn starch using a mechanical shaker and mixer for 30 minutes. The resulting mixture was compressed and formulated into tablets.

Test Example 1: In Vitro Antifungal Activity Test (MIC)

The antifungal activities of the compounds of the present invention were evaluated using *Candida albicans* as yeast fungus, and *Aspergillus fumigatus* as a filamentous fungus. The above fungi used were all purchased from American Type Culture Collection (ATCC).

The strains used in the experiment were inoculated into a Sabouraud dextrose agar medium, and then cultured at 35° C. for a sufficient period of time, e.g., 24 hours for *Candida albicans*, and about 7 days for *Aspergillus fumigatus*. As for *Candida albicans*, about 5 to 7 single colonies were taken from the cultured medium, sufficiently suspended in 1 ml of 0.85% sterile saline solution, and adjusted to have an optical density of 0.095 to 0.107 at 530 nm. A preparation of a strain diluent was diluted in Roswell park memorial institute (RPMI) 1640 medium at a 1:10 ratio, and the resultant was diluted again at a 1:100 ratio to obtain an inoculation preparation for *Candida albicans* with a concentration of 1.0×10$^3$ to 5.0×10$^3$ CFU/mL. As for *Aspergillus fumigatus*, the cultured Sabouraud dextrose agar was added with 1 mL of 0.2% Tween 20 diluted with 0.85% sterile saline solution, and then the plate was shaken to detach conidium from the plate. The solution collected from the plate surface was transferred into a sterile tube, and placed at room temperature for 5 minutes to deposit heavy substances. The resulting supernatant was transferred into the sterile tube, sufficiently suspended for about 15 seconds, and prepared a strain diluent with a concentration of 0.4×10$^6$ to 5.0×10$^6$ CFU/mL using a hemocytometer. The thus prepared strain diluent was diluted in RPMI 1640 medium at a 1:100 ratio to obtain an inoculation preparation for *Aspergillus fumigatus*. *Candida albicans* was cultured at 35° C. for 24 hours and *Aspergillus fumigatus* was cultured at 35° C. for 48 hours, and the concentrations, at which growth is inhibited by 80% or 50% compared to a negative control group, were determined using alama blue color developing reagent. All experiments were repeated twice for each concentration, and the results of antifungal activities (MIC$_{80}$ MIC$_{50}$ μg/mL) are shown in Tables 1 to 2.

TABLE 1

Result of antifungal activity (μg/mL)

| Example No. | Candida albicans MIC$_{80}$ | Aspergillus fumigatus MIC$_{50}$ |
|---|---|---|
| 1 | 0.05 | 0.1 |
| 2 | 0.02 | — |
| 3 | 0.10 | — |
| 4 | 0.11 | — |
| 5 | 0.05 | — |
| 6 | 0.10 | — |
| 7 | 0.84 | — |
| 8 | 0.24 | — |
| 9 | 1.95 | — |
| 10 | 0.04 | 0.1 |
| 11 | 0.03 | 0.05 |
| 12 | 0.22 | — |
| 13 | 0.03 | 0.44 |
| 14 | 0.06 | — |
| 15 | 0.03 | 1.95 |
| 16 | — | — |
| 17 | 0.12 | — |
| 18 | 0.03 | 0.4 |
| 19 | 0.88 | — |
| 20 | 0.22 | — |
| 21 | 0.03 | 0.5 |
| 22 | 0.23 | — |
| 23 | 0.46 | — |
| 24 | 0.06 | 1.8 |
| 25 | 0.23 | — |
| 26 | 0.06 | 1.0 |
| 27 | 0.49 | — |
| 28 | 0.12 | — |
| 29 | 0.47 | — |
| 30 | 0.31 | — |
| 31 | 0.06 | — |
| 32 | 0.03 | — |
| 33 | 0.13 | 0.5 |
| 34 | 0.25 | 1.0 |
| 35 | 0.16 | — |
| 36 | 1.31 | — |
| 37 | 0.04 | 0.3 |
| 38 | 0.02 | 0.3 |
| 39 | 0.04 | 0.7 |
| 40 | 0.04 | — |
| caspofungin | 0.25 | 0.3 |
| fluconazole | 0.25 | >32 |

'—' indicates no experiment

TABLE 2

Result of antifungal activity (μg/mL)

| Example No. | Candida albicans MIC$_{80}$ | Aspergillus fumigatus MIC$_{50}$ |
|---|---|---|
| 41 | 0.07 | — |
| 42 | 0.07 | — |
| 43 | 0.13 | — |
| 44 | 0.13 | — |
| 45 | 0.61 | — |
| 46 | 0.31 | — |
| 47 | 0.56 | — |
| 48 | 0.04 | 0.6 |
| 49 | 0.28 | 0.3 |
| 50 | 0.08 | — |
| 51 | 0.16 | — |
| 52 | 0.08 | — |
| 53 | 0.04 | 0.7 |
| 54 | 0.08 | 0.7 |
| 55 | 0.20 | — |
| 56 | 0.79 | — |
| 57 | 0.08 | — |
| 58 | 0.08 | — |
| 59 | 0.14 | — |
| 60 | 0.14 | — |
| 61 | 0.08 | — |
| 62 | 0.16 | — |
| 63 | 0.09 | — |
| 64 | 0.09 | — |
| 65 | 0.08 | — |
| 66 | 0.27 | — |
| 67 | 0.27 | — |
| 68 | 0.34 | — |
| 69 | 0.68 | — |
| 70 | 0.09 | — |
| 71 | 0.04 | — |
| 72 | 0.09 | — |
| 73 | 0.56 | — |
| 74 | 0.56 | — |
| 75 | 0.26 | — |
| 76 | 0.12 | — |
| 77 | 1.04 | — |
| 78 | 0.24 | — |
| 79 | 8.93 | — |
| 80 | — | — |
| 81 | 1.95 | — |
| caspofungin | 0.25 | 0.3 |
| fluconazole | 0.25 | >32 |

'—' indicates no experiment

As shown in Tables 1 and 2 above, the compounds of the present invention have exhibited a significantly excellent antifungal effect over the traditional antifungal agents such as caspofungin and fluconazole.

Test Example 2: In Vitro Fungicidal Activity Test (MFC, Minimum Fungicidal Concentration)

As samples of fungicidal agents, 10 mM stock solutions were diluted 10-fold by adding with RPMI 1640 medium, followed by a 5-fold serial dilution, and used as the highest concentration for evaluation of antifungal activity (MIC). The samples with the highest concentration of the fungicidal agents were treated with a 2-fold serial dilution into 11 different concentrations, and the final concentrations were determined by mixing with the strains at a 1:1 ratio. In particular, the concentration of dimethylsulfoxide used as an excipient was made to a final 1% (VN). The evaluations of the fungicidal activity of Candida albicans were performed using a test plate already completed of antifungal activity, from the highest concentration of a given sample to the concentration right next to the concentration determined to be MIC. Test solutions at each concentration were pipetted about 5 times, all were collected (about a total of 225 μL), and added into a 12-well Sabouraud dextrose agar plate. The test plate was cultured at 35° C. for 48 hours, and the minimum concentration with no fungal growth was observed with naked eyes. The result of fungicidal activity (MFC μg/mL) is shown in Table 3.

TABLE 3

Result of fungicidal activity (MFC μg/mL)

| Example No. | Candida albicans MFC |
|---|---|
| 2 | 0.1 |
| 13 | 0.1 |
| 21 | 0.1 |

TABLE 3-continued

Result of fungicidal activity (MFC μg/mL)

| Example No. | Candida albicans MFC |
|---|---|
| 37 | 0.1 |
| 38 | 0.1 |
| 39 | 0.2 |
| 40 | 0.2 |
| caspofungin | 4 |
| fluconazole | >32 |

As shown in Table 3 above, the compounds of the present invention have exhibited a significantly excellent fungicidal effect over the traditional fungicides such as caspofungin and fluconazole.

The invention claimed is:

1. A compound represented by Chemical Formula 1 below, or a pharmaceutically acceptable salt thereof:

[Chemical Formula 1]

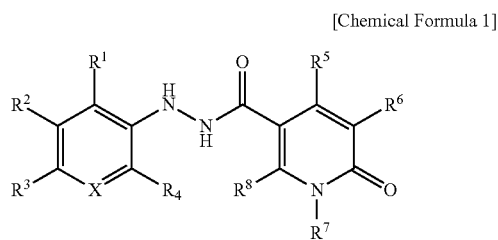

wherein,
$R^1$ is hydrogen; or halogen,
$R^2$ is hydrogen; halogen; cyano; or $C_{1-4}$ haloalkyl,
$R^3$ is hydrogen; halogen; cyano; $C_{1-4}$ alkoxy; $C_{1-4}$ haloalkyl or $C_{1-4}$ haloalkylsulfonyl,
X is carbon; or nitrogen, wherein when X is carbon, then said X is unsubstituted or substituted with halogen,
$R^4$ is hydrogen; halogen; $C_{1-4}$ alkyl; or is connected to $R^7$ to form

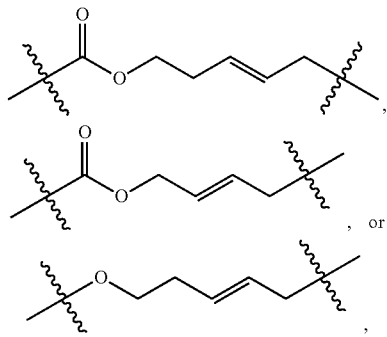

$R^5$ is hydrogen; halogen; or $C_{1-4}$ haloalkylphenylamino,
$R^6$ is hydrogen; halogen; pyridinyl; or phenyl unsubstituted or substituted with halogen, cyano, and $C_{1-4}$ haloalkyl,
$R^7$ is phenoxyethyl substituted with one to three same or different halogen atoms; phenoxyethyl substituted with $C_{1-4}$ haloalkyl; ethyl substituted with halophenyl; $C_{1-4}$ alkoxyethyl; morpholinoethyl; $C_{1-4}$ haloalkylphenylpiperazinylethyl; halophenyl; $C_{1-4}$ haloalkylphenyl; cyclohexylmethyl; thiazolylmethyl; $C_{1-4}$ haloalky-lpyridinylmethyl; $C_{1-4}$ alkyl; dimethylaminocarbonylmethyl; $C_{1-4}$ haloalkylphenylacetamido; or oxotrifluoromethylphenylethyl,
$R^8$ is hydrogen; or is connected to $R^7$ to form $C_{1-3}$ alkylene.

2. The compound or a pharmaceutically acceptable salt thereof of claim 1, wherein $R^1$ is hydrogen; chloro; or fluoro.

3. The compound or a pharmaceutically acceptable salt thereof of claim 1, wherein $R^2$ is hydrogen; chloro; fluoro; cyano; or trifluoromethyl.

4. The compound or a pharmaceutically acceptable salt thereof of claim 1, wherein $R^3$ is hydrogen; chloro; fluoro; cyano; methoxy; trifluoromethyl; or trifluoromethylsulfonyl.

5. The compound or a pharmaceutically acceptable salt thereof of claim 1, wherein $R^4$ is hydrogen; fluoro; or methyl.

6. The compound or a pharmaceutically acceptable salt thereof of claim 1, wherein $R^5$ is hydrogen; chloro; or trifluoromethylphenylamino.

7. The compound or a pharmaceutically acceptable salt thereof of claim 1, wherein $R^6$ is hydrogen; chloro; pyridinyl; chlorophenyl; fluorophenyl; cyanophenyl; or trifluoromethylphenyl.

8. The compound or a pharmaceutically acceptable salt thereof of claim 1, wherein $R^7$ is phenoxyethyl substituted with dichloro, chloro, or fluoro; trifluoromethylphenoxyethyl; chlorophenethyl; fluorophenethyl; methoxyethyl; morpholinoethyl; trifluoromethylphenylpiperazinylethyl; chlorophenyl; fluorophenyl; trifluoromethylphenyl; cyclohexylmethyl; thiazolylmethyl; trifluoromethylpyridinylmethyl; methyl; dimethylaminocarbonylmethyl; fluoromethylphenylacetamido; or oxotrifluoromethylphenylethyl.

9. The compound or a pharmaceutically acceptable salt thereof of claim 1, wherein X is carbon, said X being substituted with fluoro.

10. The compound or a pharmaceutically acceptable salt thereof of claim 1, wherein X is nitrogen,
$R^1$ is hydrogen,
$R^2$ is hydrogen or fluoro,
$R^3$ is fluoro or methoxy,
$R^4$ is hydrogen; fluoro; or methyl,
$R^5$ is hydrogen,
$R^6$ is hydrogen; chlorophenyl; fluorophenyl; cyanophenyl; or trifluoromethylphenyl, and
$R^7$ is chlorophenyl; or methyl.

11. The compound or a pharmaceutically acceptable salt thereof of claim 1, wherein $R^8$ is hydrogen; or is connected to $R^7$ to form propylene.

12. The compound or a pharmaceutically acceptable salt thereof of claim 1, wherein the compound is selected from the group consisting of:
1) N'-(2-fluorophenyl)-1-methyl-6-oxo-1,6-dihydropyridine-3-carbohydrazide,
2) N'-(3-fluorophenyl)-1-methyl-6-oxo-1,6-dihydropyridine-3-carbohydrazide,
3) N'-(4-fluorophenyl)-1-methyl-6-oxo-1,6-dihydropyridine-3-carbohydrazide,
4) N'-(3-chlorophenyl)-1-methyl-6-oxo-1,6-dihydropyridine-3-carbohydrazide,
5) N'-(4-chlorophenyl)-1-methyl-6-oxo-1,6-dihydropyridine-3-carbohydrazide,
6) N'-(3-cyanophenyl)-1-methyl-6-oxo-1,6-dihydropyridine-3-carbohydrazide,
7) N'-(4-cyanophenyl)-1-methyl-6-oxo-1,6-dihydropyridine-3-carbohydrazide,
8) 1-methyl-6-oxo-N'-(3-(trifluoromethyl)phenyl)-1,6-dihydropyridine-3-carbohydrazide, 9) 1-methyl-6-oxo-N'-(4-(trifluoromethyl)phenyl)-1,6-dihydropyridine-3-carbohydrazide,
10) 1-methyl-6-oxo-N'-(4-(trifluoromethylsulfonyl)phenyl)-1,6-dihydropyridine-3-carbohydrazide,
11) N'-(2,4-difluorophenyl)-1-methyl-6-oxo-1,6-dihydropyridine-3-carbohydrazide,
12) N'-(3,4-difluorophenyl)-1-methyl-6-oxo-1,6-dihydropyridine-3-carbohydrazide,
13) N'-(3,5-difluorophenyl)-1-methyl-6-oxo-1,6-dihydropyridine-3-carbohydrazide,
14) N'-(3,4-dichlorophenyl)-1-methyl-6-oxo-1,6-dihydropyridine-3-carbohydrazide,
15) N'-(2,4-dichlorophenyl)-1-methyl-6-oxo-1,6-dihydropyridine-3-carbohydrazide,
16) N'-(4-chloro-3-fluorophenyl)-1-methyl-6-oxo-1,6-dihydropyridine-3-carbohydrazide,
17) N'-(3-chloro-4-fluorophenyl)-1-methyl-6-oxo-1,6-dihydropyridine-3-carbohydrazide,
18) N'-(6-fluoropyridine-3-yl)-1-methyl-6-oxo-1,6-dihydropyridine-3-carbohydrazide,
19) N'-(2,6-difluoropyridine-3-yl)-1-methyl-6-oxo-1,6-dihydropyridine-3-carbohydrazide,
20) N'-(6-fluoro-2-methylpyridine-3-yl)-1-methyl-6-oxo-1,6-dihydropyridine-3-carbohydrazide,
21) N'-(5-fluoro-6-methoxypyridine-3-yl)-1-methyl-6-oxo-1,6-dihydropyridine-3-carbohydrazide,
22) 4-chloro-N'-(3-fluorophenyl)-1-methyl-6-oxo-1,6-dihydropyridine-3-carbohydrazide,
23) 4-chloro-N'-(4-fluorophenyl)-1-methyl-6-oxo-1,6-dihydropyridine-3-carbohydrazide,
24) 5-chloro-N'-(3-fluorophenyl)-1-methyl-6-oxo-1,6-dihydropyridine-3-carbohydrazide,
25) 5-chloro-N'-(4-fluorophenyl)-1-methyl-6-oxo-1,6-dihydropyridine-3-carbohydrazide,
26) 5-chloro-N'-(3-chlorophenyl)-1-methyl-6-oxo-1,6-dihydropyridine-3-carbohydrazide,
27) 5-chloro-N'-(4-chlorophenyl)-1-methyl-6-oxo-1,6-dihydropyridine-3-carbohydrazide,
28) 5-chloro-N'-(3-cyanophenyl)-1-methyl-6-oxo-1,6-dihydropyridine-3-carbohydrazide,
29) 5-chloro-N'-(4-cyanophenyl)-1-methyl-6-oxo-1,6-dihydropyridine-3-carbohydrazide,
30) 5-chloro-N'-(2,4-difluorophenyl)-1-methyl-6-oxo-1,6-dihydropyridine-3-carbohydrazide,
31) 5-chloro-N'-(3,4-difluorophenyl)-1-methyl-6-oxo-1,6-dihydropyridine-3-carbohydrazide,
32) 5-chloro-N'-(3,5-difluorophenyl)-1-methyl-6-oxo-1,6-dihydropyridine-3-carbohydrazide,
33) 7-chloro-N'-(3-fluorophenyl)-5-oxo-1,2,3,5-tetrahydroindolizine-8-carbohydrazide,
34) 7-chloro-N'-(4-fluorophenyl)-5-oxo-1,2,3,5-tetrahydroindolizine-8-carbohydrazide,
35) N'-(3-fluorophenyl)-1-methyl-6-oxo-4-(4-(trifluoromethyl)phenylamino)-1,6-dihydropyridine-3-carbohydrazide,
36) N'-(4-fluorophenyl)-1-methyl-6-oxo-4-(4-(trifluoromethyl)phenylamino)-1,6-dihydropyridine-3-carbohydrazide,
37) N'-(5-fluoro-6-methoxypyridine-3-yl)-5-(4-fluorophenyl)-1-methyl-6-oxo-1,6-dihydropyridine-3-carbohydrazide,
38) 5-(4-chlorophenyl)-N'-(5-fluoro-6-methoxypyridine-3-yl)-1-methyl-6-oxo-1,6-dihydropyridine-3-carbohydrazide,
39) N'-(5-fluoro-6-methoxypyridine-3-yl)-1-methyl-6-oxo-5-(4-(trifluoromethyl)phenyl)-1,6-dihydropyridine-3-carbohydrazide,
40) 5-(4-cyanophenyl)-N'-(5-fluoro-6-methoxypyridine-3-yl)-1-methyl-6-oxo-1,6-dihydropyridine-3-carbohydrazide,
41) N'-(3-fluorophenyl)-1-methyl-6-oxo-5-(pyridine-2-yl)-1,6-dihydropyridine-3-carbohydrazide,
42) 1-(2-fluorophenyl)-N'-(3-fluorophenyl)-6-oxo-1,6-dihydropyridine-3-carbohydrazide,
43) N',1-Bis(3-fluorophenyl)-6-oxo-1,6-dihydropyridine-3-carbohydrazide,
44) N'-(3-fluorophenyl)-1-(4-fluorophenyl)-6-oxo-1,6-dihydropyridine-3-carbohydrazide,
45) N'-(4-fluorophenyl)-6-oxo-1-(4-(trifluoromethyl)phenyl)-1,6-dihydropyridine-3-carbohydrazide,
46) N'-(4-fluorophenyl)-6-oxo-1-(3-(trifluoromethyl)phenyl)-1,6-dihydropyridine-3-carbohydrazide,
47) 1-(3-chlorophenyl)-N'-(4-fluorophenyl)-6-oxo-1,6-dihydropyridine-3-carbohydrazide,
48) 1-(3-chlorophenyl)-N'-(5-fluoro-6-methoxypyridine-3-yl)-6-oxo-1,6-dihydropyridine-3-carbohydrazide,
49) N'-(2,4-difluorophenyl)-6-oxo-1-(thiazol-4-ylmethyl)-1,6-dihydropyridine-3-carbohydrazide,
50) N'-(3-fluorophenyl)-6-oxo-1-((6-(trifluoromethyl)pyridine-3-yl)methyl)-1,6-dihydropyridine-3-carbohydrazide,
51) N'-(4-fluorophenyl)-6-oxo-1-((6-(trifluoromethyl)pyridine-3-yl)methyl)-1,6-dihydropyridine-3-carbohydrazide,
52) N'-(3,4-difluorophenyl)-6-oxo-1-((6-(trifluoromethyl)pyridine-3-yl)methyl)-1,6-dihydropyridine-3-carbohydrazide,
53) N'-(3,5-difluorophenyl)-6-oxo-1-((6-(trifluoromethyl)pyridine-3-yl)methyl)-1,6-dihydropyridine-3-carbohydrazide,
54) N'-(2,4-difluorophenyl)-6-oxo-1-((6-(trifluoromethyl)pyridine-3-yl)methyl)-1,6-dihydropyridine-3-carbohydrazide,
55) N'-(3-fluorophenyl)-6-oxo-1-(2-(4-(4-(trifluoromethyl)phenyl)piperazin-1-yl)ethyl)-1,6-dihydropyridine-3-carbohydrazide,
56) N'-(4-fluorophenyl)-6-oxo-1-(2-(4-(4-(trifluoromethyl)phenyl)piperazin-1-yl)ethyl)-1,6-dihydropyridine-3-carbohydrazide,
57) 1-(3-chlorophenethyl)-N'-(3-fluorophenyl)-6-oxo-1,6-dihydropyridine-3-carbohydrazide,
58) 1-(4-chlorophenethyl)-N'-(3-fluorophenyl)-6-oxo-1,6-dihydropyridine-3-carbohydrazide,
59) 1-(2-fluorophenethyl)-N'-(3-fluorophenyl)-6-oxo-1,6-dihydropyridine-3-carbohydrazide,
60) 1-(4-fluorophenethyl)-N'-(3-fluorophenyl)-6-oxo-1,6-dihydropyridine-3-carbohydrazide,
61) 1-(2-(2-fluorophenoxy)ethyl)-N'-(3-fluorophenyl)-6-oxo-1,6-dihydropyridine-3-carbohydrazide,
62) 1-(2-(4-chlorophenoxy)ethyl)-N'-(3-fluorophenyl)-6-oxo-1,6-dihydropyridine-3-carbohydrazide,
63) N'-(3-fluorophenyl)-6-oxo-1-(2-(3-(trifluoromethyl)phenoxy)ethyl)-1,6-dihydropyridine-3-carbohydrazide,
64) 1-(2-(2,4-dichlorophenoxy)ethyl)-N'-(3-fluorophenyl)-6-oxo-1,6-dihydropyridine-3-carbohydrazide,
65) 1-(2-(4-fluorophenoxy)ethyl)-N'-(3-fluorophenyl)-6-oxo-1,6-dihydropyridine-3-carbohydrazide,
66) 1-(cyclohexylmethyl)-N'-(3-fluorophenyl)-6-oxo-1,6-dihydropyridine-3-carbohydrazide,
67) 1-(cyclohexylmethyl)-N'-(4-fluorophenyl)-6-oxo-1,6-dihydropyridine-3-carbohydrazide, 68) N'-(3-fluorophenyl)-6-oxo-1-(2-oxo-2-(4-(trifluoromethyl)phenyl)ethyl)-1,6-dihydropyridine-3-carbohydrazide,
69) N'-(4-fluorophenyl)-6-oxo-1-(2-oxo-2-(4-(trifluoromethyl)phenyl)ethyl)-1,6-dihydropyridine-3-carbohydrazide,
70) N'-(3,4-difluorophenyl)-6-oxo-1-(2-oxo-2-(4-(trifluoromethyl)phenyl)ethyl)-1,6-dihydropyridine-3-carbohydrazide,
71) 2-(5-(2-(3-fluorophenyl)hydrazinecarbonyl)-2-oxopyridine-1(2H)-yl)-N-(4-(trifluoromethyl)phenyl)acetamide,
72) 2-(5-(2-(4-fluorophenyl)hydrazinecarbonyl)-2-oxopyridine-1(2H)-yl)-N-(4-(trifluoromethyl)phenyl)acetamide,
73) N'-(3-fluorophenyl)-1-(2-morpholinoethyl)-6-oxo-1,6-dihydropyridine-3-carbohydrazide,
74) N'-(4-fluorophenyl)-1-(2-morpholinoethyl)-6-oxo-1,6-dihydropyridine-3-carbohydrazide,
75) 2-(5-(2-(3-fluorophenyl)hydrazine-1-carbonyl)-2-oxopyridine-1(2H)-yl)-N,N-dimethylacetamide,
76) N'-(3-fluorophenyl)-1-(2-methoxyethyl)-6-oxo-1,6-dihydropyridine-3-carbohydrazide,
77) 2-(5-(2-(4-fluorophenyl)hydrazinecarbonyl)-2-oxopyridine-1(2H)-yl)-N,N-dimethylacetamide,
78) N'-(4-fluorophenyl)-1-(2-methoxyethyl)-6-oxo-1,6-dihydropyridine-3-carbohydrazide,
79) $(1^5E,10E)$-$5^5$-fluoro-$1^1$,$1^2$-dihydro-7-oxa-3,4-diaza-1(5,1)-pyridina-5(1,2)-benzenacyclododecaphan-10-ene-$1^2$,2,6-trione,
80) $(1^5E,9E)$-$1^1$,$1^2$-dihydro-7-oxa-3,4-diaza-1(5,1)-pyridina-5(1,2)-benzenacycloundecaphan-9-ene-$1^2$,2,6-trione, and
81) $(1^5E,9E)$-$1^1$,$1^2$-dihydro-6-oxa-3,4-diaza-1(5,1)-pyridina-5(1,2)-benzenacycloundecaphan-9-ene-12,2-dione.

13. A pharmaceutical composition comprising a compound or a pharmaceutically acceptable salt thereof according to claim 1 as an active ingredient, and a pharmaceutically acceptable carrier or vehicle.

14. A pharmaceutical composition for treatment of fungal infectious diseases caused by *Candida albicans* or *Aspergillus fumigatus*, comprising a compound or a pharmaceutically acceptable salt thereof according to claim 1 as an active ingredient, and a pharmaceutically acceptable carrier or vehicle.

15. A method for treatment of fungal infectious diseases caused by *Candida albicans* or *Aspergillus fumigatus* comprising administering a composition comprising a compound or a pharmaceutically acceptable salt thereof according to claim 1 as an active ingredient, and a pharmaceutically acceptable carrier or vehicle to a subject with the fungal infectious disease or a subject suspected of having the same.

\* \* \* \* \*